(12) United States Patent
Sachdeva et al.

(10) Patent No.: US 8,647,661 B1
(45) Date of Patent: Feb. 11, 2014

(54) SURFACE MODIFIED MULTILAYERED NANOSTRUCTURES FOR DERMAL DELIVERY

(75) Inventors: Mandip Sachdeva, Tallahassee, FL (US); Punit Shah, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 13/289,733

(22) Filed: Nov. 4, 2011

Related U.S. Application Data

(60) Provisional application No. 61/410,547, filed on Nov. 5, 2010.

(51) Int. Cl.
*A61Q 19/00* (2006.01)

(52) U.S. Cl.
USPC ........... 424/443; 977/706; 977/737; 977/740; 977/906

(58) Field of Classification Search
None
See application file for complete search history.

(56) References Cited

U.S. PATENT DOCUMENTS

| | | | |
|---|---|---|---|
| 7,112,340 B2 * | 9/2006 | Kipp et al. | 424/489 |
| 2003/0072793 A1 * | 4/2003 | Frey et al. | 424/449 |
| 2004/0058006 A1 * | 3/2004 | Barry et al. | 424/489 |
| 2006/0110439 A1 | 5/2006 | Tobia et al. | |
| 2006/0171917 A1 * | 8/2006 | Campbell et al. | 424/85.1 |
| 2007/0093420 A1 * | 4/2007 | Yeomans et al. | 514/12 |
| 2007/0212528 A1 | 9/2007 | Mackay et al. | |
| 2008/0206341 A1 * | 8/2008 | Gasco | 424/489 |
| 2008/0318837 A1 * | 12/2008 | Quay et al. | 514/2 |
| 2009/0285869 A1 * | 11/2009 | Trimble | 424/401 |
| 2009/0324955 A1 | 12/2009 | Mohanty et al. | |
| 2010/0136124 A1 | 6/2010 | Prestidge et al. | |

FOREIGN PATENT DOCUMENTS

| | | |
|---|---|---|
| WO | 2005084326 | 9/2005 |
| WO | 2007128066 | 11/2007 |
| WO | 2010120420 | 10/2010 |

OTHER PUBLICATIONS

Badea, I. Gemini Cationic Surfactant-Based Delivery Systems for Non-Invasive Cutaneous Gene Therapy. Thesis, University of Saskatchewan, Degree of Doctor of Philosophy in the College of Pharmacy and Nutrition, copyright May 2006.

Kim, B.-S.; Kim, C.-S.; Lee, K.-M. The Intracellular Uptake Ability of Chitosan-coated Poly (D,L-lactide-co-glycolide) Nanoparticles. Arch Pharm Res. vol. 31, No. 8, pp. 1050-1054, Jun. 2008.

(Continued)

*Primary Examiner* — Ernst Arnold
*Assistant Examiner* — Jianfeng Song
(74) *Attorney, Agent, or Firm* — Nilay J. Choksi; Smith & Hopen, P.A.

(57) ABSTRACT

Dermal delivery is best suited for the various skin diseases or disorders. However, the stratum corneum limits the permeation of number of suitable pharmaceutical agents for dermal delivery. Certain embodiments of the present invention include surface modified multilayered nanostructures. The modification was completed by using fatty acids enabling delivery of a significant amount of one or more pharmaceutical agent(s) into deeper layers of the epidermis and dermis to treat skin diseases or disorders. Each active pharmaceutical agent can be encapsulated into the separate layers of the nanostructures.

17 Claims, 10 Drawing Sheets

(56) References Cited

OTHER PUBLICATIONS

Figure 1:
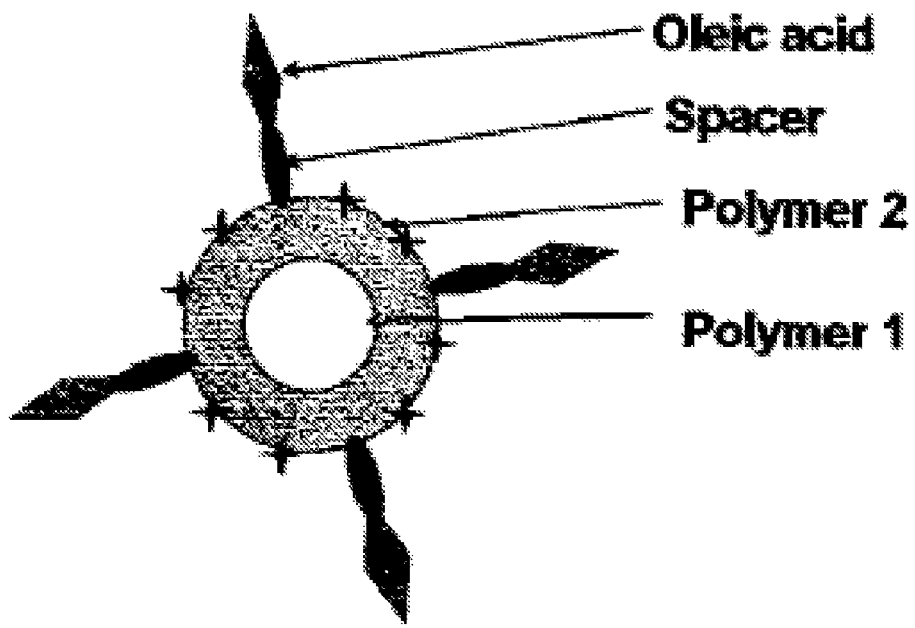
Figure 2:
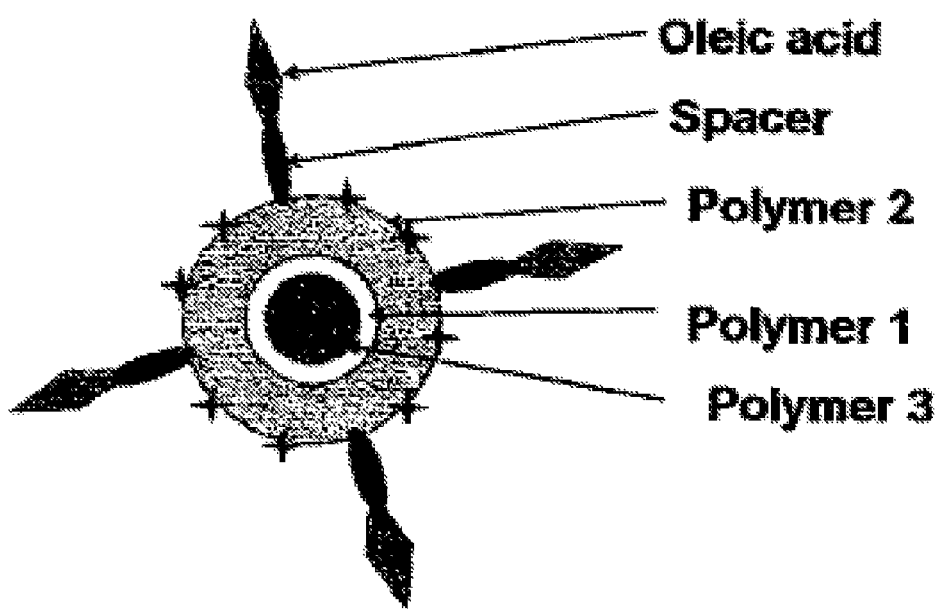
Figure 3:
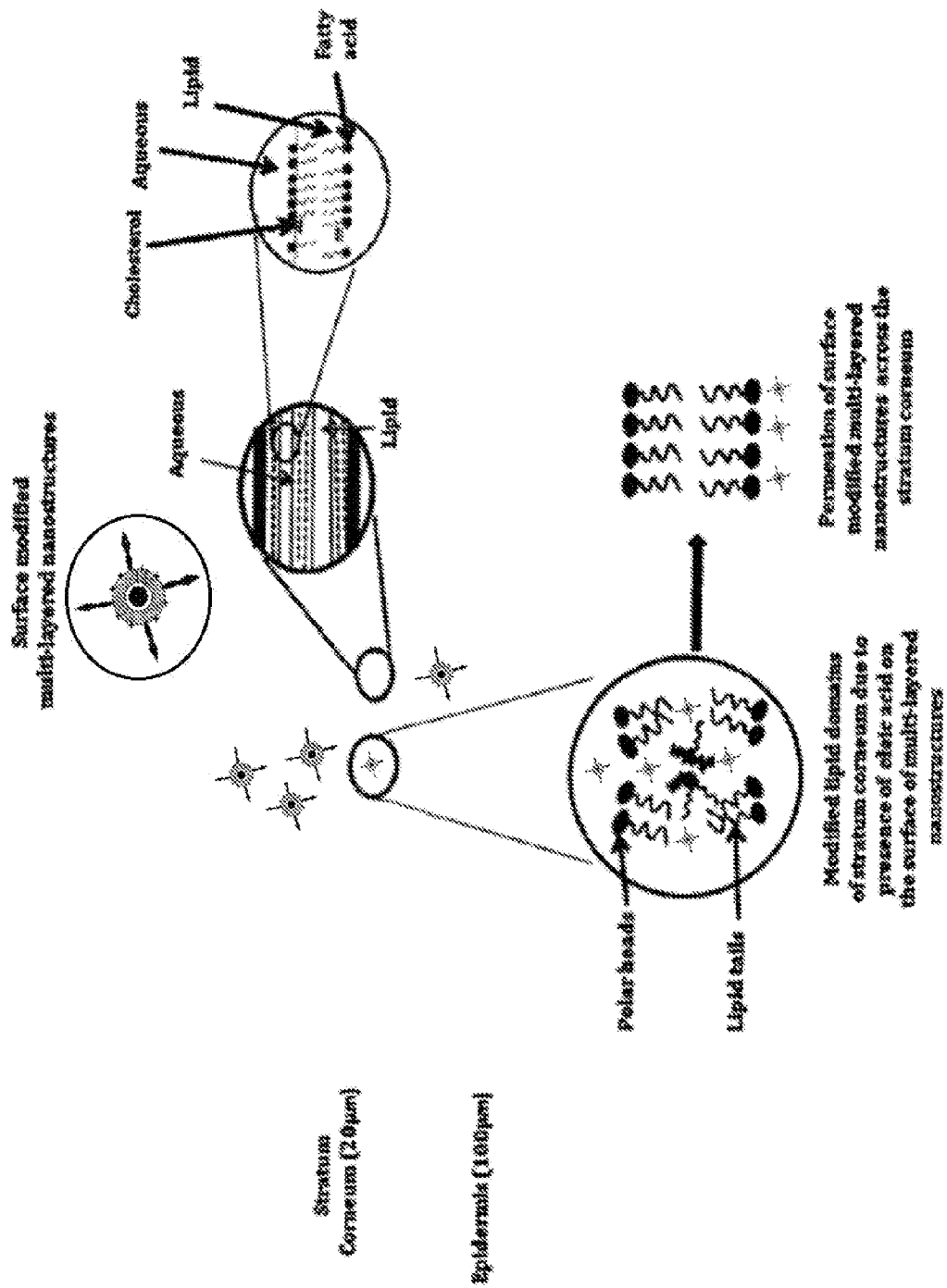

Taetz, S.; Nafee, N.; Beisner, J.; Piotrowska, K.; Baldes, C.; Murdter, T.E.; Huwer, H.; Schneider, M.; Schaefer, U.F.; Klotz, U.; Lehr, C.-M. THe influence of chitosan content in cationic chitosan/PLGA nanoparticles on the delivery efficiency of antisense 2'-O-methyl-RNA directed against telomerase in lung cancer cells. European Journal of Pharmaceutics and Biopharmaceutics. 72, pp. 358-369, 2009.

Kumar, M.N.V.R.; Bakowsky, U.; Lehr, C.M. Preparation and characterization of cationic PLGA nanospheres as DNA carriers. Biomaterials. 25, pp. 1771-1777, 2004.

Ali, A.M.I.; Mayes, A.G. Preparation of Polymeric Core-Shell and Multilayer Nanoparticles: Surface-Initiated Polymerization Using in Situ Synthesized Photoiniferters. Macromolecules. 43, pp. 837-844, 2010.

Nafee, N.; Schneider, M.; Schaefer, U.F.; Lehr, C.-M. Relevance of the colloidal stability of chitosan/PLGA nanoparticles on their cytotoxicity profile. International Journal of Pharmaceutics. 381, pp. 130-139, 2009.

Guan, X.-P.; Quan, D.-P.; Liao, K.-R.; Wang, T.; Xiang, P.; Mai, K.-C. Preparation and Characterization of Cationic Chitosan-modified Poly(D,L-lactide-co-glycolide) Copolymer Nanospheres as DNA Carriers. Journal of Biomaterials Applications. 22, pp. 353-371, 2008.

Gupta, R.; Yadav, P.; Saraf, S.A. Polyelectrolyte multilayer assembly bearing ketoprofen for transdermal delivery. Power Point Presentation, XVIIth International Conference on Bioencapsulation, Groningen, Netherlands, Sep. 24-26, 2009.

Gittins, D.I.; Caruso, F. Multilayered Polymer Nanocapsules Derived from Gold Nanoparticle Templates. Advanced Materials. 12:24, pp. 1947-1949, 2000.

Lee, P.-W.; Hsu, S.-H.; Tsai, J.-S.; Chen, F.-R.; Huang, P.-J.; Ke, C.-J.; Liao, Z.-X.; Hsiao, C.-W.; Lin, H.-J.; Sung, H.-W. Multifunctional core-shell polymeric nanoparticles for transdermal DNA delivery and epidermal Langerhans cells tracking. Biomaterials. 31, pp. 2425-2434, 2010.

Yang, R.; Yang, S.-G.; Shim, W.-S.; Cui, F.; Cheng, G.; Kim, I.-W.; Kim, D.-D.; Chung, S.-J.; Shim, C.-K. Lung—Specific Delivery of Paclitaxel by Chitosan-Modified PLGA Nanoparticles Via Transient Formation of Microaggregates. Journal of Pharmaceutical Sciences. 98:3, pp. 970-984, 2009.

Zhou, J.; Romero, G.; Rojas, E.; Ma, L.; Moya, S.; Gao, C. Layer by layer chitosan/alginate coatings on poly (lactide-co-glycolide) nanoparticles for antifouling protection and Folic acid binding to achieve selective cell targeting. Journal of Colloid and Interface Science. 345, pp. 241-247, 2010.

Jain, T.K.; Morales, M.A.; Sahoo, S.K.; Leslie-Pelecky, D.L.; Labhasetwar, V. Iron Oxide Nanoparticles for Sustained Delivery of Anticancer Agents. Molecular Pharmaceutics. 2:3, pp. 194-205, 2005.

Nafee, N.; Taetz, S.; Schneider, M.; Schaefer, U.F.; Lehr, C.-M. Chitosan-coated PLGA nanoparticles for DNA/RNA delivery: effect of the formulation parameters on complexation and transfection of antisense oligonucleotides. Nanomedicine: Nanotechnology, Biology, and Medicine. 3, pp. 173-183, 2007.

Huang, H.; Yang, X. Chitosan mediated assembly of gold nanoparticles multilayer. COlliods and Surfaces A; Physicochem. Eng. Aspects. 226, pp. 77-86, 2003.

* cited by examiner

SURFACE MODIFIED MULTILAYERED NANOSTRUCTURES FOR DERMAL DELIVERY

CROSS-REFERENCE TO RELATED APPLICATIONS

This application claims priority to U.S. Provisional Application No. 61/410,547, entitled "Surface Modified Multilayered Nanostructures for Dermal Delivery," filed on Nov. 5, 2010, the contents of which are hereby incorporated by reference into this disclosure.

FEDERALLY SPONSORED RESEARCH OR DEVELOPMENT

This invention was made with Government support under Grant No. G12RR03020 awarded by Research Centers in Minority Institutions awarded by the National Institute of Health. The government has certain rights in the invention.

BACKGROUND OF THE INVENTION

1. Field of the Invention

This invention relates, generally, to the delivery of pharmaceutical agents. More particularly, it relates to dermal delivery of active pharmaceutical agent(s) by surface modified multilayered nanostructures penetrating the stratum corneum.

2. Description of the Prior Art

Dermal delivery of pharmaceutical agent(s) has several advantages over conventional oral and intravenous dosage forms for treatment of skin diseases when the target site is present in the deep epidermis. Delivering pharmaceutical agents dermally avoids the first pass effect, allows local delivery of the drug, minimizes a patient's pain and avoids excessive drug dumping into the blood associated with other dosage forms (B. W. Barry, Novel mechanisms and devices to enable successful transdermal drug delivery, *Eur. J. Pharm. Sci.,* 14 (2001) 101-114). Dermal delivery is best suited for skin diseases and disorders, including: fungal, bacterial and viral infections; inflammation associated with rheumatoid arthritis, Crohn's disease, multiple sclerosis, eczema and psoriasis; tumor and dry skin; dermatitis and skin cancers like melanoma; etc. It is also desirable to deliver many cosmetic and active pharmaceutical agent(s) to have anti-wrinkle and/or anti-aging effects.

To treat such skin diseases and disorders, the effective delivery of active pharmaceutical agent(s) into the deeper layers of skin is needed. However, the stratum corneum, or foremost layer of skin, acts as the main barrier between the body and the environment, thereby limiting the delivery of many drugs (B. W. Barry, Novel mechanisms and devices to enable successful transdermal drug delivery, *Eur. J. Pharm. Sci.,* 14 (2001) 101-114; K. Moser et al., Passive skin penetration enhancement and its quantification in vitro, *Eur. J. Pharm. Biopharm.,* 52 (2001) 103-112). To deliver sufficient amount of the active pharmaceutical agent(s) into the deeper layers of skin, many techniques have been introduced and performed, for example chemical enhancement including permeation enhancers and prodrug design (K. B. Sloan, Prodrugs for dermal delivery, *Adv. Drug Deliv. Rev.,* 3 67-101; J. Drustrup et al., Utilization of prodrugs to enhance the transdermal absorption of morphine, *Int. J. Pharm.,* 71 (1991) 105-116), physical enhancement including use of microneedles (M. R. Prausnitz, Microneedles for transdermal drug delivery, *Adv. Drug Deliv. Rev.,* 56 (2004) 581-587), ionotophoresis (Y. N. Kalia et al., Iontophoretic drug delivery, *Adv. Drug Deliv. Rev.,* 56 (2004) 619-658), phonophoresis, thermal modulation, magnetic modulation, mechanical modulation, ultrasound (N. B. Smith, Applications of ultrasonic skin permeation in transdermal drug delivery, *Expert Opin. Drug Deliv.,* 5 (2008) 1107-1120), and electroporation (A. R. Denet et al., Skin electroporation for transdermal and topical delivery, *Adv. Drug Deliv. Rev.,* 56 (2004) 659-674). However, each of these techniques has its respective problems in terms of toxicity and therapeutic feasibility.

Nanotechnology is an advanced and non-invasive technique adopted for improving skin permeation of active pharmaceutical agent(s) (T. W. Prow et al., Nanoparticles and microparticles for skin drug delivery, *Adv. Drug Deliv. Rev.,* 63 (2011) 470-91). Various biocompatible and biodegradable synthetic or semi-synthetic polymers, including polylactic acid (PLA) (F. Rancan et al., Investigation of polylactic acid (PLA) nanoparticles as drug delivery systems for local dermatotherapy, *Pharm. Res.,* 26 (2009) 2027-2036), poly(lactic-co-glycolic acid) (PLGA) (J. Lademann et al., Nanoparticles—an efficient carrier for drug delivery into the hair follicles, *Eur. J. Pharm. Biopharm.,* 66 (2007) 159-164), poly (ϵ-caprolactone) (R. Alvarez-Roman et al., Biodegradable polymer nanocapsules containing a sunscreen agent: preparation and photoprotection, *Eur. J. Pharm. Biopharm.,* 52 (2001) 191-195), and chitosan (C. Colonna et al., Ex vivo evaluation of prolidase loaded chitosan nanoparticles for the enzyme replacement therapy, *Eur. J. Pharm. Biopharm.,* 70 (2008) 58-65) have shown promise in dermal delivery, including topical and transdermal drug delivery.

Several studies have been reported on preparation and characterization of polymeric biodegradable nanoparticles as skin delivery systems due to their potential usefulness in increasing efficacy, reducing enzymatic degradation, controlling release rates and high encapsulation efficiency (F. Rancan et al., Investigation of polylactic acid (PLA) nanoparticles as drug delivery systems for local dermatotherapy, *Pharm. Res.,* 26 (2009) 2027-2036; J. Lademann et al., Nanoparticles—an efficient carrier for drug delivery into the hair follicles, *Eur. J. Pharm. Biopharm.,* 66 (2007) 159-164; R. Alvarez-Roman et al., Biodegradable polymer nanocapsules containing a sunscreen agent: preparation and photoprotection, *Eur. J. Pharm. Biopharm.,* 52 (2001) 191-195; R. Alvarez-Roman et al., Enhancement of topical delivery from biodegradable nanoparticles, *Pharm. Res.,* 21 (2004) 1818-1825; X. Wu et al., Disposition of nanoparticles and an associated lipophilic permeant following topical application to the skin, *Mol. Pharm.,* 6 (2009) 1441-1448).

The most commonly used polymer for the preparation of these carriers is PLGA. PLGA is well known to be safe, biocompatible, non-toxic and is restorable through natural pathways (J. Panyam et al., Biodegradable nanoparticles for drug and gene delivery to cells and tissue, *Adv. Drug Deliv. Rev.,* 55 (2003) 329-347). Further, chitosan is a promising and often used candidate for surface modification due to its biocompatibility (P. P. Shah et al., Influence of chitosan crosslinking on bitterness of mefloquine hydrochloride microparticles using central composite design, *J. Pharm. Sci.,* 98 (2009) 690-703) and positive charge (D. Vllasaliu et al., Tight junction modulation by chitosan nanoparticles: comparison with chitosan solution, *Int. J. Pharm.,* 400 (2010) 183-193). Studies have shown that chitosan and its derivatives interact with the negative charge of SC resulting in opening of tight junctions (S. F. Taveira et al., Effect of the iontophoresis of a chitosan gel on doxorubicin skin penetration and cytotoxicity, *J. Control Release,* 134 (2009) 35-40; W. He et al., Study on the mechanisms of chitosan and its derivatives used as transdermal penetration enhancers, *Int. J. Pharm.*, 382 (2009) 234-243; W. He et al., Transdermal permeation enhancement of N-trimethyl chitosan for testosterone, Int. J. Pharm., 356 (2008) 82-87), thus acting as a permeation enhancer.

Though the polymer-based nanoparticles offer advantage of controlled and sustained drug release with greater stability (R. Alvarez-Roman et al., Enhancement of topical delivery from biodegradable nanoparticles, *Pharm. Res.*, 21 (2004) 1818-1825; X. Wu et al., Disposition of nanoparticles and an associated lipophilic permeant following topical application to the skin, *Mol. Pharm.*, 6 (2009) 1441-1448; S. Kuchler et al., Nanoparticles for skin penetration enhancement—a comparison of a dendritic core-multishell-nanotransporter and solid lipid nanoparticles, *Eur. J. Pharm. Biopharm.*, 71 (2009) 243-250), they have not been explored to a greater extent for dermal delivery.

Moreover, studies have indicated that nanoparticles do not cross the stratum corneum but rather permeate into the layers of the stratum corneum and release the drug in a controlled manner into the upper epidermis, followed by passive diffusion to further skin layers. This limits the amount of active pharmaceutical agent(s) that actually reaches the target region.

Nanoparticles have also been noted to accumulate in skin furrows and permeate through hair follicles with their associated sebaceous glands, rather than crossing the stratum corneum (SC) (F. Rancan et al., Investigation of polylactic acid (PLA) nanoparticles as drug delivery systems for local dermatotherapy, *Pharm. Res.*, 26 (2009) 2027-2036). Thus, the amount of active pharmaceutical agent(s) actually reaching the target site is very limited. (R. R. Patlolla et al., Translocation of cell penetrating peptide engrafted nanoparticles across skin layers, *Biomaterials*, 31 (2010) 5598-5607; A. Vogt et al., 40 nm, but not 750 or 1,500 nm, Nanoparticles Enter Epidermal CD1a+ Cells after Transcutaneous Application on Human Skin, *J. Invest. Dermatol.*, 126 (2006) 1316-1322; R. Alvarez-Roman et al., Skin penetration and distribution of polymeric nanoparticles, *J. Control Release*, 99 (2004) 53-62). In addition, only a small amount of active pharmaceutical agent(s) permeates into the hair follicle in the first place.

Many scientists have reports use of bilayered polymeric nanoparticles, such as chitosan modified poly(D,L-lactide-co-glycolide) (PLGA) copolymer nanoparticles for improving DNA and siRNA delivery into the cells (N. Nafee et al., Chitosan-coated PLGA nanoparticles for DNA/RNA delivery: effect of the formulation parameters on complexation and transfection of antisense oligonucleotides. *Nanomedicine* 3 (2007) 173-183; M. N. Ravikumar et al., Preparation and characterization of cationic PLGA nanospheres as DNA carriers. *Biomaterials* 25 (2004) 1771-1777).

Similarly, Zhou et al. reports use of multilayered nanoparticles, alginate and chitosan to coat PLGA nanoparticles for folic acid binding to achieve selective cell targeting. The surface of these multilayered nanoparticles is modified by folic acid through polyethylene glycol. These folic acid-modified multilayered nanoparticles showed improved cell uptake (J. Zhou et al., Layer by layer chitosan/coatings on poly(lactide-co-glycolide) nanoparticles for antifouling protection and folic acid binding to achieve selective cell targeting. *J. Colloid Interface Sci.* 345 (2010) 241-247).

Jain et al. reported use of water-dispersible oleic acid-poloxamer-coated iron oxide magnetic nanoparticle formulation to load high doses of water insoluble anticancer drug. In this study, oleic acid was used to dissolve the water-insoluble anticancer drug, and the surface of the magnetic nanoparticles was modified by poloxamers. The role of oleic acid was to keep iron oxide magnetic core inside the co-polymer matrix. These magnetic nanoparticles showed sustained intracellular retention and dose-dependent antiproliferative effect in breast and cancer cell lines (T. K. Jain et al., Iron oxide nanoparticles for sustained delivery of anticancer agents. *Mol. Pharm.* 2 (2005) 194-205).

A study has also reported use of bilayered polymeric nanoparticles for transdermal delivery of DNA and epidermal Langerhans cells tracking. However, this study used gene gun bombardment technique for delivery of DNA into the deeper skin layers (P. W. Lee et al. Multifunctional core-shell polymeric nanoparticles for transdermal DNA delivery and epidermal Langerhans cells tracking *Biomaterials* 31 (2010) 2425-2434). This gene gun bombardment technique is an aggressive approach for dermal delivery and requires special assistance.

Fatty acids (FA) are known to be chemical permeation enhancers and widely used in commercial formulations. FA interacts with, induces and modifies the lipid domains within the stratum corneum bilayer lipids (B. W. Barry, Mode of action of penetration enhancers in human skin, *J. Control Release*, 6 (1987) 85-97). Electron microscopic study has suggested that lipid domain is stimulated within the SC bilayer lipids upon exposure to oleic acid (OA), a well-known fatty acid (H. Tanojo et al., In vitro human skin barrier perturbation by oleic acid: Thermal analysis and freeze fracture electron microscopy studies, *Thermochimica Acta*, 293 (1997) 77-85). The formation of such induced pools provides permeability defects within the bilayer lipids, thus facilitating permeation through the membrane into the deeper layers of skin.

Furthermore, with increasing complexities of these skin-related diseases and disorders, application of only one active pharmaceutical agent does not always treat the disease or disorder effectively. In addition, to achieve a therapeutic response, higher doses of a drug are required, resulting in unwanted side effects. To overcome this problem, a combination therapy is used to treat various disease conditions because the combination of disease modifying drugs can act through different pathways and offer possibility of synergistic or additive effects (C. Zegpi et al., The effect of opioid antagonists on synergism between dexketoprofen and tramadol, *Pharmacol. Res.*, 60 (2009) 291-295), thus minimizing drug induced toxicities associated with higher dose of individual drug. However, the art has not shown any studies attempting to deliver more than one active pharmaceutical agent dermally using surface modified multilayered nano structures.

Accordingly, what is needed is the effective simultaneous delivery of two or more active pharmaceutical agent(s) into the deeper layers of skin without use of special techniques, such as gene gun bombardment. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, more effective and lower cost method of delivering two or more pharmaceutical agents dermally is now met by a new, useful and nonobvious invention.

In a first embodiment, the present invention includes a composition for dermal delivery of at least one pharmaceutical agent, the composition comprising at least one pharmaceutical agent admixed with at least one layer of nanostructures. The layer(s) of nanostructures is modified by a spacer linked to a fatty acid, allowing penetration of the stratum corneum.

Figure 10A:
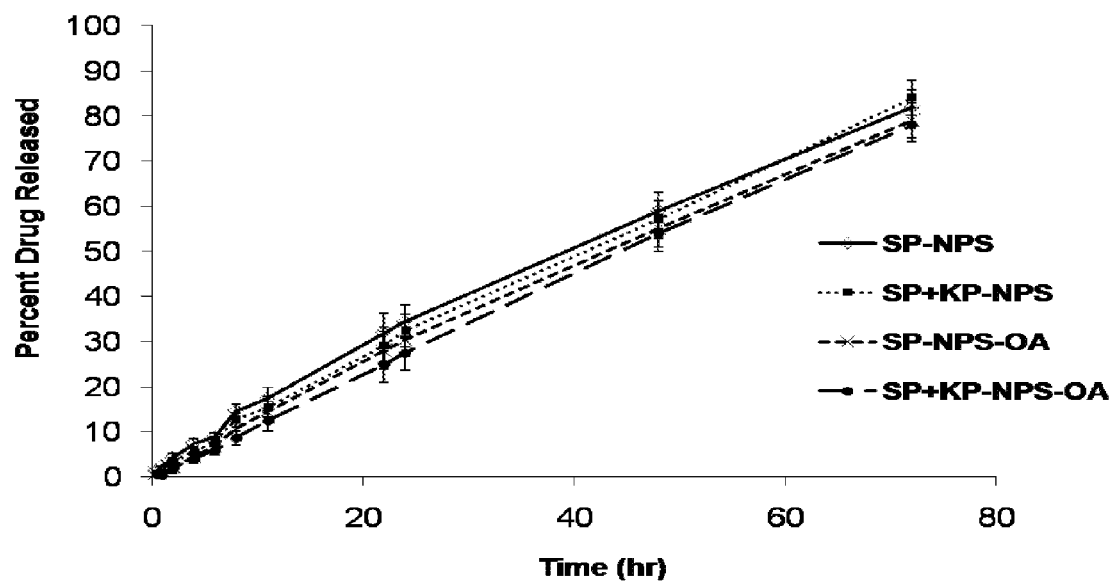
Figure 10B:
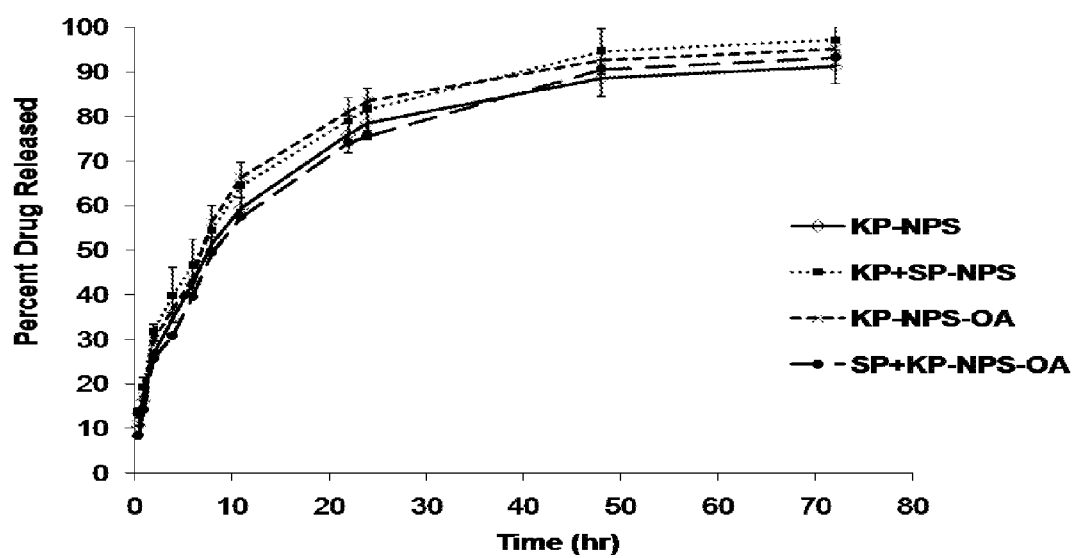
Figure 11:
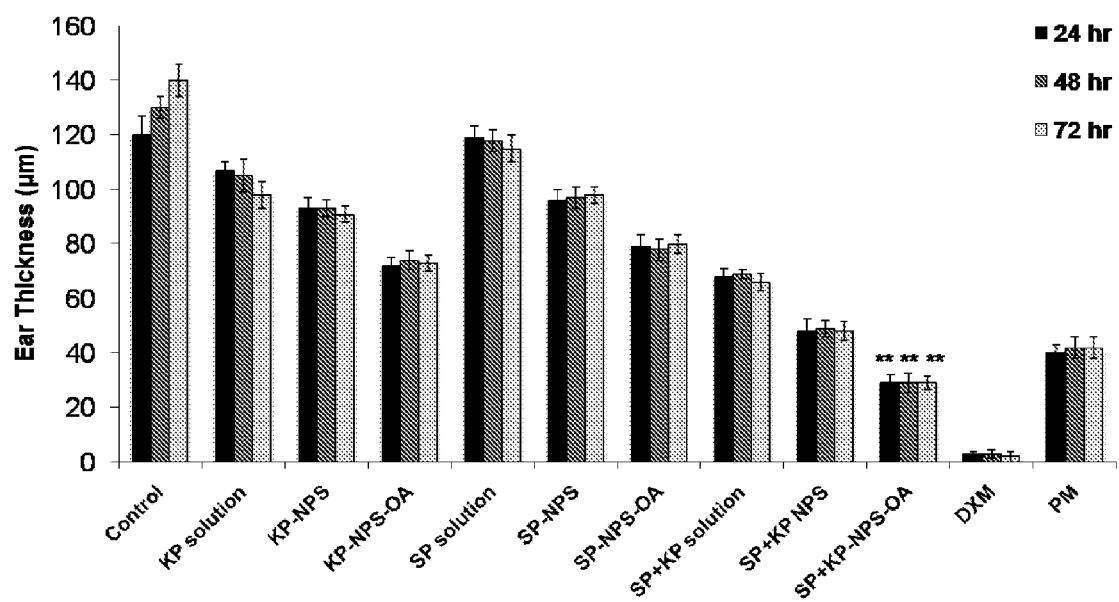
Figure 12:
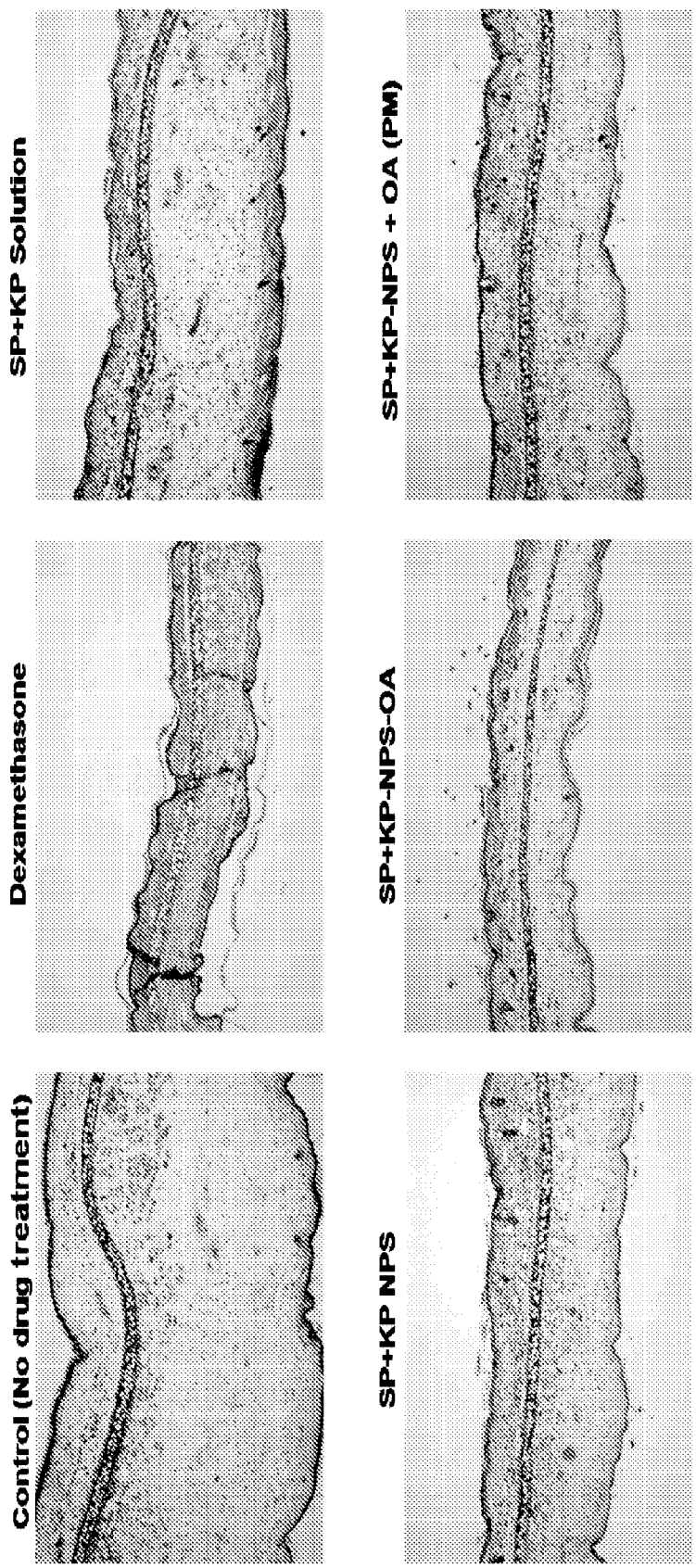

In a further embodiment, the spacer contains a hydrocarbon chain having a multiple bond and an R group selected from hydrogen, alkyl, aklenyl, alkynyl, alkoxy, hydroxyalkyl, hydroxyl and haloalkyl. In another embodiment, the spacer may be selected from modified polyethylene glycols, propylene glycols, amino acids, peptides, chelators and polaxamers.

In a further embodiment, the fatty acid linked to the spacer is oleic acid.

In a further embodiment, the at least one pharmaceutical agent is selected from spantide II, cyclosporine A, alpha-MSH, capsaicin and ketoprofen.

In another embodiment, the composition further comprises a polymer. The polymer may be PLGA.

In another embodiment, the composition further comprises a lipid. The lipid may be a derivative of glycerol.

In yet another embodiment, the composition further comprises an emulsifying agent. The emulsifying agent may be polyvinyl alcohol.

In another embodiment, the further composition comprises a surfactant. The surfactant may be tween 80.

In yet another embodiment, the composition further comprises an anti-foaming agent. The anti-foaming agent may be span 80.

In another embodiment, the composition further comprises a cross-linking agent. The cross-linking agent may be tripolyphosphate or glutaraldehyde.

In a separate embodiment, the present invention contemplates a carrier for dermal delivery of at least one pharmaceutical agent, wherein the carrier comprises the pharmaceutical agent and at least one layer of surface modified nanostructures, collectively admixed with a carrier agent, resulting in a carrier. The carrier can be an aqueous dispersion, nanogel, lotion, powder, liniment, ointment, cream or patch.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 1 depicts an embodiment of surface modified multi-layered nanostructures prepared using two (2) polymers;

FIG. 2 depicts an embodiment of surface modified multi-layered nanostructures using three (3) polymers;

FIG. 3 depicts a mechanism of skin permeation of an embodiment of the surface modified multilayered nanostructures;

FIG. 4 depicts the mechanism by which chitosan and OA-PEG are combined for further modification of the surface of the nanoparticles;

FIG. 5A depicts graphically the effect of amount of PLGA on the particle size and zeta potential of the NPS;

FIG. 5B depicts graphically the effect of amount of chitosan on the particle size and zeta potential of the NPS;

FIG. 6 depicts in vitro rat skin permeation of lipophilic DiO fluorescent dye encapsulated NPS with and without OA. Vertical row indicates the depth of skin sections. The left panel indicates that in the sections of DiO-NPS permeated skin, fluorescence was observed up to 160 μm (white arrow). The right panel indicates that in the sections of DiO-NPS-OA permeated skin, fluorescence was observed up to 240 μm (white arrow);

FIG. 7 depicts a graphical comparison of the percent fluorescence percent intensity of the DiO-NPS and DiO-NPS-OA permeated skin sections using confocal laser scanning microscopy. The percent fluorescence intensity of the images were plotted against the skin depth for both OA modified and un-modified DiO-NPS. Data represent mean±SEM (n=6); significance DiO-NPS-OA against DiO-NPS, $^{**}p<0.001$;

FIG. 8 depicts a graphical comparison of in vitro rat skin permeation of DID-NPS and DID-NPS-OA using Raman confocal spectroscopy. The fluorescence intensity of each section was plotted for different depths of the skin. Data represent mean±SEM (n=6); significance DID-NPS-OA against DID-NPS, $^{**}p<0.001$;

FIG. 9A depicts a graphical comparison illustrating the effect of OA on the skin permeation of SP encapsulated NPS. Data represent mean±SEM, n=6; significance NPS-OA against NPS, NPS+OA (PM) and solution, $^{**}p<0.001$;

FIG. 9B depicts a graphical comparison illustrating the amount of KP retained by the skin after 24 hours in the different skin layers. The data represent the amount of KP per gram of skin for different formulations of KP. Data represent mean±SEM, n=6; significance NPS-OA against NPS, NPS+OA (PM) and solution, $^{**}p<0.001$;

FIG. 9C is a graphical comparison illustrating the amount of KP permeated through dermatomed human skin in vitro into receiver compartment. The total amount of KP per unit area of skin was plotted for OA modified and un-modified KP- and SP+KP-NPS. Data represent mean±SEM, n=6; significance NPS-OA against NPS, $^{**}p<0.001$;

FIG. 10A depicts graphically in vitro drug release of SP from NPS in phosphate buffer saline, PBS (pH 7.4) containing 0.5% w/v Volpo. The released amount of SP alone without OA, with KP and without OA, SP alone with OA, and with KP and with OA was plotted against time from SP-NPS and SP-NPS-OA along with SP+KP-NPS and SP+KP-NPS-OA. Data represent mean±SEM, n=6;

FIG. 10B depicts graphically in vitro drug release of KP from NPS in PBS (pH 7.4) containing 0.5% w/v Volpo. The released amount of KP from KP-NPS and KP-NPS-OA along with SP+KP-NPS and SP+KP-NPS-OA alone without OA, with SP and without OA, KP alone with OA, and with SP and KP with OA was plotted against time. Data represent mean±SEM, n=6;

FIG. 11 depicts graphically the effect of SP and KP solutions, surface modified and unmodified nanoparticles, along with the physical mixture of oleic acid-PEG and unmodified nanoparticles containing SP and KP together on the reduction of allergic contact dermatitis in C57/BL mice. Data represent mean±SEM, n=6; significance NPS-OA against NPS, NPS+OA (PM)OA modified NPS against OA unmodified, physical mixture and solution, **$p<0.001$;

FIG. 12 depicts histological staining of ACD induced C57/BL mice ears after treatment with a positive control dexamethasone (DXM) and a combination of SP and KP comprising NPS and NPS-OA. The images were taken using a 10× lens.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Certain embodiments of the present invention relate to dermal delivery of surface modified multilayered nanostructures containing active pharmaceutical agent(s) into the deeper layers of skin. As used herein, the terms "nanostructure" and "nanoparticle" may be used interchangeably to refer to any polymeric micelle, lipid micelle, hybrid lipid-polymer micelle, liposome, niosomes, transferosome, liponanoparticle, lipid nanoparticles, nanostructured lipid nanocarriers (NLC), solid lipid nanoparticles (SLN), hybrid lipid-polymer nanostructures, bicelle, polymerosomes, lamellar structures, and lipid vesicles, among other delivery systems that can be used suitably to deliver one or more active pharmaceutical agent(s).

The surface of multilayered nanostructure is modified using spacer linked to fatty acid which enables transport of multilayered nanostructures by crossing the stratum corneum, thus delivering active pharmaceutical agent(s) into the deeper layers of skin. These multilayered nanoparticles can be used for the delivery of two (2) or more active pharmaceutical agent(s). Each polymeric or lipid matrix comprises an active pharmaceutical agent.

Examples of polymers used to prepare multilayered nanostructures include, but are not limited to, lipids or oils, gelatin, sodium alginate, gum arabic, starch, tragacanth, shellac, paraffin wax, poly(lactide-co-glycolide) (PLGA), polylactic acid (PLA), polycaprolactone (PCL), methyl cellulose, pectin, carrageenan, alginates, methyl cellulose, casein, bovine albumin serum, chitosan, hydroxypropyl cellulose, hydroxypropyl methyl cellulose, ethyl cellulose, cellulose acetate phthalate, carmellose, polyvinyl alcohol, polystyrene, polyurethane, polyvinylpyrrolidone, polymethacrylate, polyvinyl acetate, polyhydroxyethyl methacrylate, polyvinyl chloride, polyacrylate, polyacrylamide, polyethylene glycol, polyester, polyurea, and polyamide, among other suitable polymers that may be used to prepare multilayered nanostructures.

Examples of lipids that may be used include, but are not limited to, derivatives of glycerophospholipids, glycerolipids, sphingolipids, sterols, fatty acyl amides, prenols, ceramides, cholesterols, lecithin, glyceryl behenate (COMPRITOL), glyceryl palmitostearate (PRECIROL), glycerol monosterol (MONOSTEROL), glycerol disterate, sulfatides, phosphosphingolipids, phosphatidylcholines, phosphatidic acids, phosphatidylethanolamines, phosphatidylglycerols, phosphatidylserines, and phosphor lipids, among other suitable lipids that may be used to prepare multilayered nanostructures.

Examples of oils that may be used include, but are not limited to, safflower oil, sesame oil, corn oil, castor oil, coconut oil, almond oil, cotton seed oil, soybean oil, olive oil, mineral oil, spearmint oil, clove oil, lemon oil, peppermint oil, triacetin, tributryin, ethyl butyrate, ethyl caprylateoleic acid, ethyl oleate, isopropyl myristate and ethyl caprylate, among other suitable oils that may be used to prepare multilayered nanostructures.

A combination of polymer and/or lipid can be used to prepare multilayered nanoparticles. Two or more polymers or lipids may be used to prepare multilayered nanoparticles. The multilayered nanoparticles can be prepared using electrostatic interaction, self-assembly, ionotropic gelation, cross-linking, coacervation, homogenization-solvent evaporation, sonication, ultrasound, nanoprecipitation, spray drying, high pressure homogenization, layer by layer, freeze drying, hot-melt homogenization, film formation, co-solvent evaporation, high pressure instruments such as NANODEBEE, and coating or solvent emulsion methods, in combination or alone.

Examples of antifoaming agents include, but are not limited to, ethylene glycol fatty acid ester, span 65, span 85, propylene glycol monostearate, glyceryl monostearate etc. Examples of emulsifying agents and surfactants include but limited to sorbitan monopalmitate, sorbitan monostearate, sodium laurate, triethanolamine oleate, potassium stearate, triethanolamine stearate, sorbitan sesquioleate, sorbitan monolaurate, sodium oleate, propylene glycol monostearate, polyoxyethylene laurylether, polyoxyethylene sorbitan monopalmitate, polyoxyethylene sorbitan monolaurate, polyoxyethylene sorbitan monooleate, bezalkonium chloride, polyethylene glycol monostearate, cetrimide, glyceryl monostearate, alkylpolyoxyethylene sulfate, lecithin, polyvinyl alcohol, and sodium lauryl sulfate.

The surface of the multilayered nanoparticles can be modified with spacer linked to fatty acid, enabling enhanced transport of multilayered nanostructures across the stratum corneum. Examples of fatty acids that may be used as skin permeation enhancers include, but are not limited to, oleic acid, stearic acid, palmitic acid, sapienic acid, palmitoleic acid, myristoleic acid, linoleic acid, linoelaidic acid, linolenic acid, lauric acid, myristic acid, stearic acid, behenic acid, capric acid, caprylic acid, lignoceric acid, cerotic acid, vaccenic acid, and octadecenoic acids, among other suitable fatty acids. Further examples of spacers that can be used include, but are not limited to, hydrocarbon chains having one or more double bonds or triple bonds. More specifically, spacers may be modified or unmodified polyethylene glycols, propylene glycols, amino acids, peptides, chelators and polaxamers, among other known suitable spacers. Examples of chelators include, but are not limited to, saccharides, urea, DTPA, methyl cellulose, polyvinyl pyrrolidone, 1,2-Dioleoylsn-glycero-3-[(N-(5-amino-1-carboxypentyl)imidodiacetic acid) succinyl nickel salt] (DGS-NTA (Ni)) and EDTA, among other suitable chelators.

If a hydrocarbon chain is present, the hydrocarbon chain can be interrupted by —O—, —S—, —N(R)—, —N(R)—C(O)—O—, —O—C(O)—N(R)—, —O—C(O)—O—N (R)—, —N(R)—C(O)—N(R)—, —O—C(O)—O—, —P(R)—, —P(O)(R)—, and —C(O)—O(R)—. Each R, independently, is aliphatic or aromatic. If aromatic, the compounds may include two (2) or more membered rings with or without heteroatoms.

Examples of R include, but are not limited to, hydrogen, alkyl, alkenyl, alkynyl, alkoxy, hydroxylalkyl, hydroxyl, and haloalkyl.

The interrupted hydrocarbon chain can be used for conjugation with each polymer or lipid.

Succinimidyl ester of fatty acid coupled to spacer can be used due to undergo a simple incubation reaction with free amine groups of polymers or lipids. The polymer(s) or lipid (s) can be modified for amine group using chemical reaction, if required. In addition, the fatty acid can be attached to each layer of nanostructures by chemical reaction using a suitable spacer. For example, one end of the spacer (e.g., PEG) can be modified with oleic acid (OA), while the other end is modified with succinimidyl ester.

The surface modified multilayered nanostructures can be dispersed via a variety of carriers, including, but not limited to, aqueous dispersion, gel, lotion, powder, liniment, emulsion, ointment, cream and patch.

Certain embodiments of the present invention also include one or more active pharmaceutical agents. Generally, active pharmaceutical agents comprise small molecules, proteins or peptides alone or in combination with one or more small molecules, or proteins or peptides alone or in combination with each other.

More specifically, examples of active pharmaceutical agents include, but are not limited to, anti-inflammatory agents, anti-psoriatic agents, analgesic agents, anti-parasitic agents, anti-cancer agents, anti-bacterial agents, anti-fungal agents, anti-viral agents, anti-aging agents, anti-wrinkle agents, anti-acne agents, immunomodulators, proteins and peptides, nucleosides, nucleotides, enzymes, hormones, vitamins, zinc oxide, titanium oxide UV-A absorbers, UV-B absorbers, and natural compounds used for cosmetic purposes. Other suitable active pharmaceutical agents may be used, given their usefulness in treating a disease or disorder related to the skin or associated tissue layers. If proteins are used, suitable proteins include, but are not limited to, deoxyribonucleic acid, small interfering ribonucleic acid, and oligonucleotides.

The active pharmaceutical agent(s), with multilayered nanoparticles, is delivered to the skin, including the stratum corneum and the other layers of the epidermis and dermis. In one embodiment, the active pharmaceutical agent(s) is delivered primarily to the epidermis at a depth of more than eighty (80) microns.

Drug release from the multilayered nanostructure can be immediate release or controlled release for each drug from each layer of multilayered nanostructures. Particular polymers and/or lipids can be selected for immediate or controlled release of each drug from each layer of multilayered nano structures.

Dermal delivery includes transdermal, topical, intramuscular, intradermal, and/or subcutaneous delivery of the active pharmaceutical agent(s). Techniques that may be used to perform dermal delivery include, but are not limited to, injection, microneedles, electroporation, sonophoresis, ultrasound, phonophoresis, thermal modulation, magnetic modulation, mechanical modulation and ionophoresis, among other suitable known techniques.

Example 1

A. Preparation of Bilayered Nanostructures (NPS)

In one embodiment, an organic phase is created comprising PLGA and a first active pharmaceutical agent dissolved in dichloromethane. This organic phase is added to an aqueous phase comprising polyvinyl alcohol, polyoxyethylene (20) sorbitan monooleate (TWEEN 80), sorbitan monooleate (SPAN 80), and chitosan or gelatin to form an emulsion. This emulsion can be broken down into nanodroplets by applying external energy. Forms of external energy include, but are not limited to, homogenization and sonication.

The nanodroplets form nanostructures upon evaporation of the highly volatile organic solvent contained in the nanodroplets. The solvent can be evaporated during magnetic stirring of the nanodroplets at about 300 rpm under atmospheric conditions for about four (4) hours. The evaporation leaves behind a colloidal dispersion.

A cross-linking agent, selected in this embodiment specifically for chitosan or gelatin, can be chosen. Examples include sodium tripolyphosphate, or glutaraldehyde. This cross-linking agent was mixed with a second active pharmaceutical agent. The resultant mixture was added drop-wise to the colloidal dispersion to form multilayered nanostructures. To complete cross linking, the colloidal dispersion was stirred at about 300 rpm for about two (2) hours.

B. Surface Modification of NPS Using Oleic Acid

In an embodiment, the multilayered nanostructures resulting from the first step is mixed with OA-PEG-succinimidyl ester for about two (2) to four (4) hours at room temperature. The pH of the reaction mixture can be adjusted to 8 using phosphate buffer. The resulting surface modified multilayered nanostructure can then be dialyzed against de-ionized water using dialysis tubing for about 24 hours.

Figure 4:
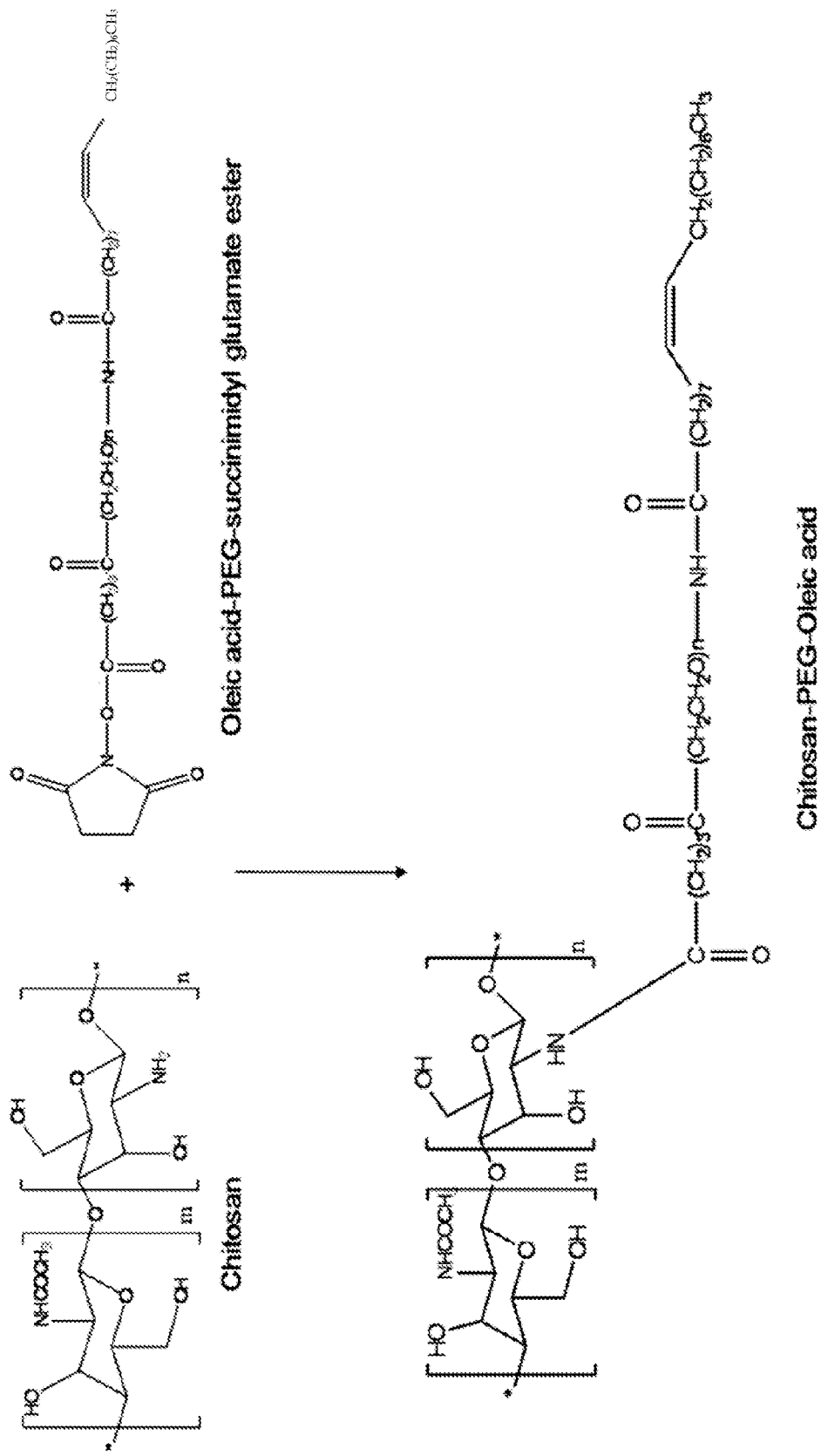

FIG. 4 depicts the mechanism by which the surface of NPS was modified with OA. In a first step, the oleic acid-PEG-succinimidyl ester reacts with free amine groups of the chitosan present on the surface of NPS. In a second step, a covalent amide bond forms between the chitosan and PEG derivative by releasing N-hydroxysuccinimide. At the end of the reaction the surface of NPS was modified with OA using PEG as a spacer.

Example 2

A. Materials

PLGA was purchased from PURAC biomaterials (Lincolnshire, Ill.). Polyvinyl alcohol (PVA), low molecular weight chitosan (molecular weight—50 kDa; 75-85% degree of deacetylation), dichloromethane, tween 80, sodium tripolyphosphate (TPP), polyethylene glycol 400 (PEG-400), phosphate buffer saline (PBS, pH 7.4), sodium bicarbonate ($NaHCO_3$), bovine serum albumin (BSA), trifluoroacetic acid (TFA), dexamethasone, 2,4,6-trinitrobenzene sulfonic acid (TNBS) and 2,4-dinitrofluorobenzene (DNFB) were purchased from SIGMA-ALDRICH Co. (St. Louis, Mo.). HPLC grade of acetonitrile, dichloromethane, water and ethanol were purchased from SIGMA-ALDRICH Co. (St Louis, Mo.). OA-PEG-succinimidyl glutarate ester was custom synthesized from NANOCS Inc. (New York, N.Y.). Ketoprofen (KP) was purchased from SPECTRUM CHEMICALS & LABORATORY PRODUCTS (Gardena, Calif.). Spantide II (SP) was purchased from AMERICAN PEPTIDE COMPANY, Inc. (Sunnyvale, Calif.). Hoechst 34580, DID and DiO dyes were purchased from INVITROGEN Corporation (Eugene, Oreg.). PEG-1000 was chosen and obtained as the linker/spacer.

B. Animals

Hairless rats (CD® (SD) HrBi, Male) and C57BL/6 mice (6 weeks old, male) were obtained from CHARLES RIVER LABORATORIES (Wilmington, Mass.). They were grouped and housed (n=6 per cage) in cages with bedding. The animals were kept under controlled conditions of a 12:12 hour light:dark cycle, 22° C.±2° C. and 50±15% RH. The mice were kept on diets from HARLAN TEKLAD and water ad libitum. The animals were housed at FLORIDA AGRICULTURAL AND MECHANICAL UNIVERSITY (Tallahassee, Fla.) which has AAALAC-accredited facilities. The animals were acclimatized to laboratory conditions for one week prior to experimentation.

C. Preparation of Nanoparticles

1. Preparation of Nanoparticles without SP and/or KP

Multilayered nanoparticles (NPS) were prepared by modified emulsion solvent evaporation method (X. Yuan et al., The development and mechanism studies of cationic chitosan-modified biodegradable PLGA nanoparticles for efficient siRNA drug delivery, *Pharm Res*, 27 (2010) 1285-1295). Ten (10) mg of PLGA was dissolved in 1.5 ml of dichloromethane. This organic phase was added to 20 ml of 0.1% w/v PVA solution comprising 4 ml of 0.5% w/v chitosan and 1.5 ml of tween 80 with constant stirring to form an emulsion.

This emulsion was broken down into nanodroplets by homogenization for fifteen (15) minutes at 30,000 rpm. The nanodroplets were stirred for thirty (30) minutes to evaporate the organic phase, thus forming the nanostructures. Five (5) ml of the NPS dispersion was transferred to a separate vial.

The chitosan, present on the outer layer of NPS was then cross-linked with 100 μl of 1% w/v TPP to promote the bilayered NPS formation. The resultant NPS dispersion was stirred at 300 rpm for two (2) hours for complete cross-linking of chitosan.

2. Preparation of Nanoparticles with SP and/or KP

To prepare SP nanoparticles (SP-NPS), five (5) mg of SP was dissolved in 100 μl of ethanol and then mixed with the organic phase containing PLGA. NPS were prepared by homogenization, using a substantially similar procedure as described above. To this nanoparticle dispersion, 1% w/v TPP was added for cross-linking of chitosan coat. To prepare SP and KP nanoparticles (SP+KP-NPS), KP was dispersed in 1% w/v TPP and added drop wise to SP containing bilayered nanoparticles (SP-NPS). To prepare KP nanoparticles (KP-NPS), SP was excluded from the NPS preparation procedure.

Fluorescent nanoparticles (DiO/DID-NPS) were prepared by incorporating DiO/DID dye in PLGA core by dissolving it in dichloromethane, maintaining a substantially similar procedure as described above.

KP Solution, SP Solution and a combination of SP+KP solution (SP+KP-Solution) were prepared by dissolving drugs in 100 μl ethanol. To this combined solution, oleic acid was added and volume adjusted with PEG-400.

D. Surface Modification of Nanoparticles (NPS-OA)

For surface modification, 1 ml of NPS was suspended in 500 μl of phosphate buffer pH 7.4. Then OA with succinimidyl glutamate ester side group (the mole ratio of chitosan to OA was varied as 1:2, 1:4 and 1:6), previously dissolved in 10 μl of DMSO, was incubated for different time intervals with constant stirring to complete the N-hydroxysuccinimide reaction. The surface-modified NPS were represented as KP-NPS-OA, SP-NPS-OA and SP+KP-NPS-OA for KP, SP and a combination of SP and KP, respectively.

FIG. 4 depicts the mechanism by which the surface of NPS was modified with OA. The outer layer of the NPS was composed of chitosan. In a first step, the oleic acid-PEG-succinimidyl glutarate ester reacts with amine groups of the chitosan present on the surface of NPS. This involves hydrolysis of ester linkage by slightly increasing pH to 7.4 in phosphate buffer. In a second step, a covalent amide bond forms between the chitosan and PEG derivative by releasing N-hydroxysuccinimide. At the end of the reaction the surface of NPS was modified with OA using PEG as a spacer.

E. TNBS Method

TNBS method was performed to estimate the percent of surface-accessible amino groups by colorimetric reaction. The NPS and NPS-OA were dispersed in distilled water and incubated with 4% w/v $NaHCO_3$ and 0.1% w/v TNBS reagent at room temperature for two (2) hours with constant stirring.

The reaction mixture was then centrifuged at 13,500 rpm for ten (10) minutes and the absorbance of the supernatant was measured at 420 nm using a spectrophotometer (M200 TECAN, San Jose, Calif.). For control, the distilled water was used in place of NPS, following the same procedure.

F. Characterization of NPS

The particle size and zeta potential of NPS and NPS-OA were measured using NICOMP 380 ZLS (PARTICLE SIZING SYSTEMS, Port Richey, Fla.). The NICOMP 380 ZLS analyzer uses dynamic light scattering to obtain the essential features of the particle size distribution. The assay of SP and KP was performed by dissolving 100 μl of NPS or NPS-OA in 900 μl of ethanol. The samples were then centrifuged at 13,000 rpm for fifteen (15) minutes, and 100 μl of supernatant was injected into WATERS high-performance liquid chromatography (HPLC).

The mean particle sizes of KP-NPS, SP-NPS and SP+KP-NPS were found to be 153, 173 and 169 nm, respectively, with polydispersity indices (PI) from 0.12 to 0.18. The mean particle size of SP+KP-NPS-OA was increased from 183 to 217 nm because of increase in mole ratio of chitosan:OA.

TABLE 1 depicts the effect of different amounts of OA incubation with NPS.

| Nanoparticles | Particle Size (nm) | Polydispersity Index | Zeta Potential (mV) | Surface-accessible amine group of nanoparticles modified after 2h of incubation with OA (%) |
|---|---|---|---|---|
| SP + KP-NPS-OA (1:2) | 183 ± 22 | 0.24 | 10.43 ± 2.21 | 54.65 ± 4.68 |
| SP + KP-NPS-OA (1:4) | 194 ± 17 | 0.21 | 7.59 ± 1.74 | 66.83 ± 3.28 |
| SP + KP-NPS-OA (1:6) | 217 ± 19 | 0.29 | 5.34 ± 1.43 | 81.90 ± 3.43 |

NPS were incubated with OA for two (2) hours. As the amount of OA increased on the surface of the NPS, the particle size also increased. In addition, as the amount of OA increased on the surface of the NPS, zeta potential decreased. This is due to the amino groups of the chitosan on the surface of NPS occupied in the formation of amide linkage.

Figure 5A:
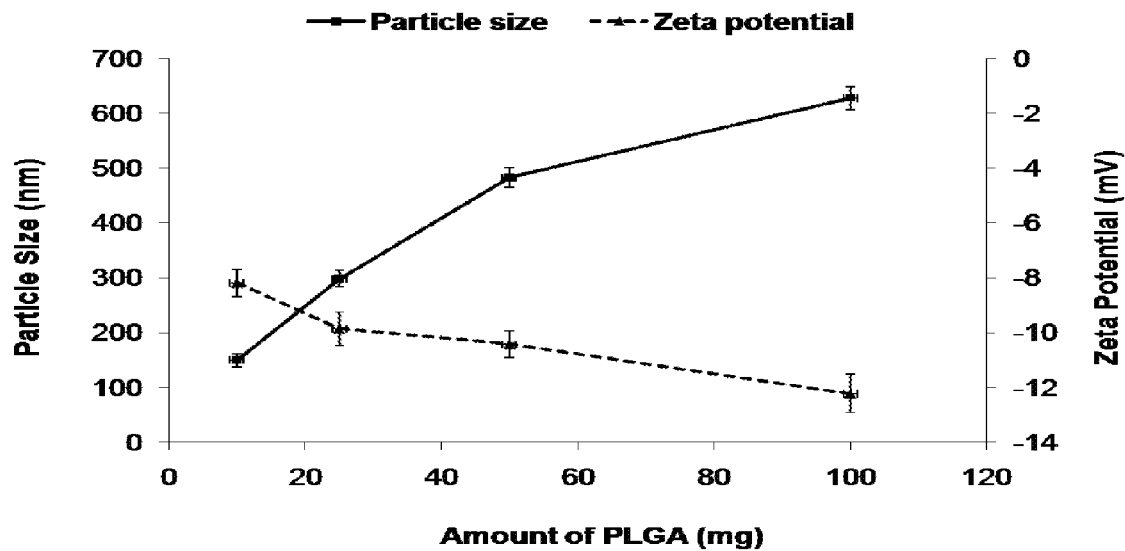

The zeta potentials of KP-NPS, SP-NPS and SP+KP-NPS in double distilled water were 11.17, 13.82 and 16.76 mV, respectively. The PLGA nanoparticles without chitosan coat had a negative zeta potential, as depicted in FIG. 5A. As the amount of PLGA was increased from 10 mg to 100 mg, particle size increased and zeta potential decreased.

Figure 5B:
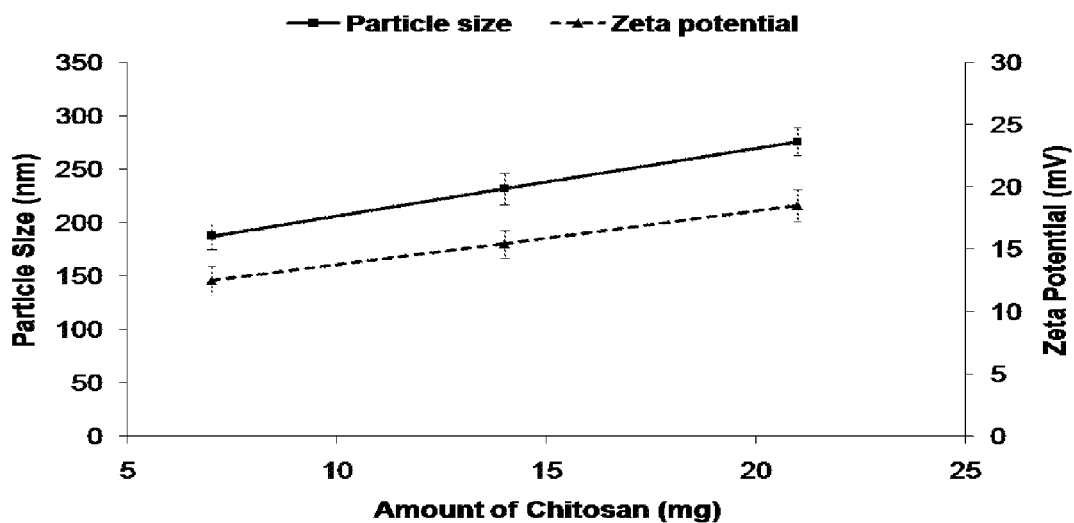

Zeta potential values of the chitosan-shelled nanoparticles were positive owing to their cationic chitosan coat, as depicted in FIG. 5B. As the amount of chitosan increased, the zeta potential increased. However, the zeta potential of SP+KP-NPS-OA decreased from 10.43 to 5.34 mV, possibly caused by reduction in free amine groups of chitosan, available on the surface of nanoparticles.

Entrapment efficiency was determined using vivaspin columns, with a molecular weight cut-off (MWCO) of 10,000 Da (R. R. Patlolla et al., Translocation of cell penetrating peptide engrafted nanoparticles across skin layers, Biomaterials, 31 (2010) 5598-5607). The NPS and NPS-OA (0.5 ml) were placed on top of the vivaspin centrifuge filter membrane and centrifuged at 4,500 rpm for fifteen (15) minutes. The amount of SP and KP present in the aqueous phase was estimated using HPLC.

The entrapment efficiencies of SP and KP were found to be 92.81%±2.17% and 81.27%±2.26%, respectively. The entrapment efficiency of SP and KP was unaffected by surface modification. According to TNBS method, 82% of surface accessible amino groups of chitosan were modified.

G. Confocal Laser Scanning Microscopy (CLSM)

CLSM measures skin permeation of a compound. Studies with DiO-NPS and DiO-NPS-OA were performed using rat skin as described by Patlolla et al (R. R. Patlolla et al., Translocation of cell penetrating peptide engrafted nanoparticles across skin layers, Biomaterials, 31 (2010) 5598-5607). The DiO-NPS and DiO-NPS-OA were applied to the epidermal side in the donor compartment of Franz diffusion cell. The receiver compartment was filled with PBS (pH 7.4) Skin permeation studies were performed at 32° C.±0.5° C. After 24 hours, the dosing area (0.64 cm$^2$) was collected using biopsy punch.

To visualize the skin-associated fluorescence, thin lateral serial skin sections (about 40 μm to about 240 μm) were collected using cryotome (SHANDON SCIENTIFIC Ltd., England). For nuclei staining, the skin sections were incubated with the Hoechst dye solution (1 μg/μl), prepared in PBS (pH 7.4) for thirty (30) minutes without light.

The sections were then washed two times with PBS (pH 7.4) Skin sections were visualized with a laser confocal microscope (LEICA MICROSYSTEMS Inc., Buffalo Grove, Ill.) using 10× objective. The instrument settings were kept constant for DiO-NPS-OA and DiO-NPS treated samples. Finally, the collected images were analyzed using digital image software for the skin-associated fluorescence.

Figure 6:
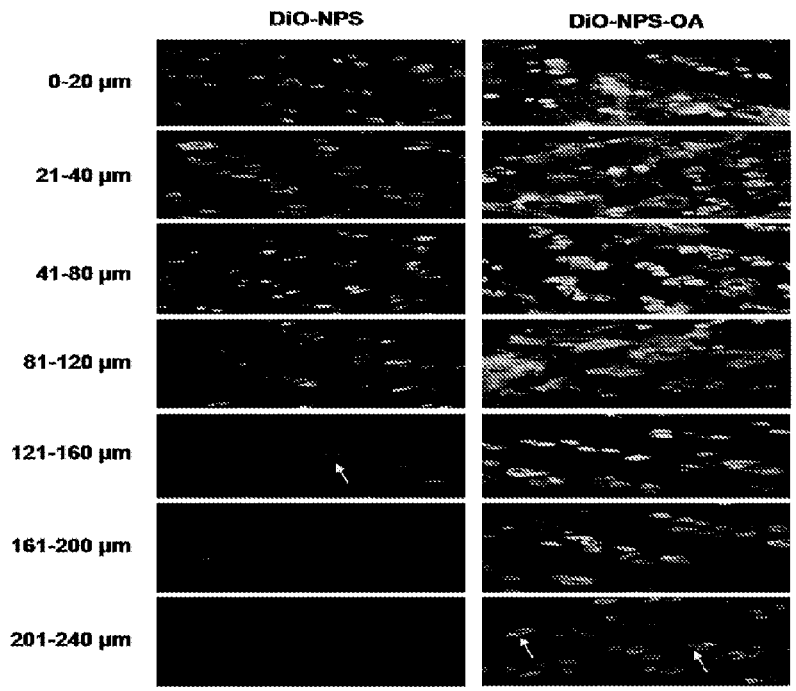

After 24 hours of skin permeation of DiO-NPS and DiO-NPS-OA, the lateral skin sections were made to a depth of 240 μm with cryotome and observed under confocal laser scanning microscope for skin associated fluorescence. The fluorescence from the DiO-NPS was seen to decrease with increase in skin depth. Intense fluorescence for DiO-NPS was observed up to 120 μm; decreased fluorescence for DiO-NPS was observed at up to 160 μm; fluorescence for DiO-NPS was diminished at further depths, as depicted in FIG. 6. However, the fluorescence from DiO-NPS-OA treated skin was detectable at a skin depth of up to 240 μm, also depicted in FIG. 6.

Figure 7:
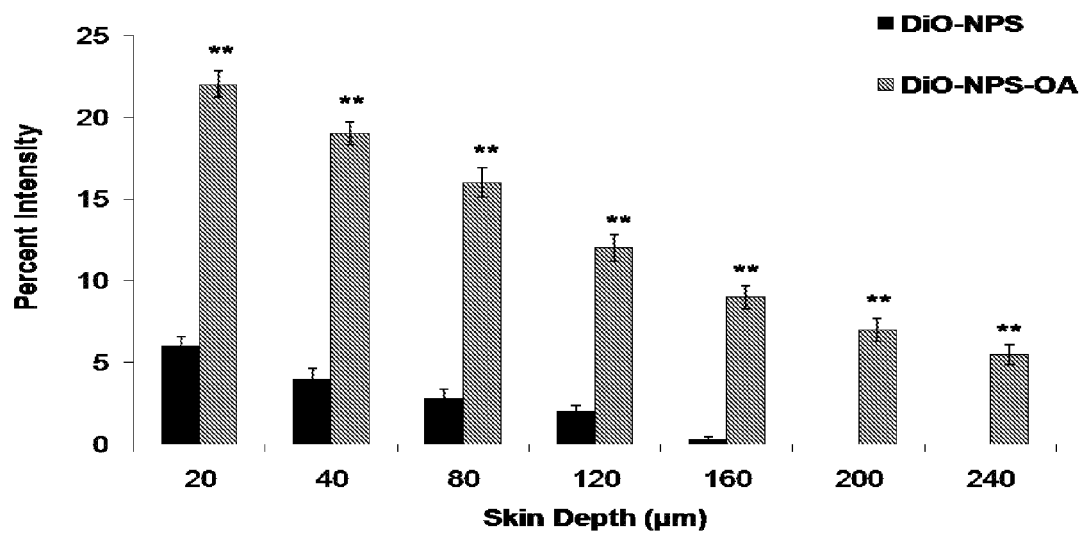

The difference between the percent intensities of confocal microscopic images for DiO-NPS and DiO-NPS-OA was evaluated using digital image software, shown graphically in FIG. 7. The percent intensity of DiO-NPS-OA was approximately 4 times higher than DiO-NPS at various depths.

H. Raman Confocal Spectroscopy

Lateral rat skin sections of the DID-NPS and DID-NPS-OA were collected using a substantially similar procedure as explained for CLSM and were observed with HR800 Raman spectroscopy (HORIBA Jobin Yvon, Edison, N.J.) for fluorescence intensity by positioning the skin sections on the microscope stage.

Raman confocal spectroscopy was calibrated and set as reported by Patlolla et al (R. R. Patlolla, P. R. Desai, K. Belay, M. S. Singh, Translocation of cell penetrating peptide engrafted nanoparticles across skin layers, Biomaterials, 31 (2010) 5598-5607). The fluorescence data were acquired using 10× objective and a 200 mm confocal pin hole. For control, the Raman spectrum of untreated rat skin sections was collected as a function of depth up to 240 μm. Raman spectra of DID-NPS and DID-NPS-OA in skin permeation samples were acquired over an approximate range of 200 cm$^{-1}$ to 1600 cm$^{-1}$.

Figure 8:
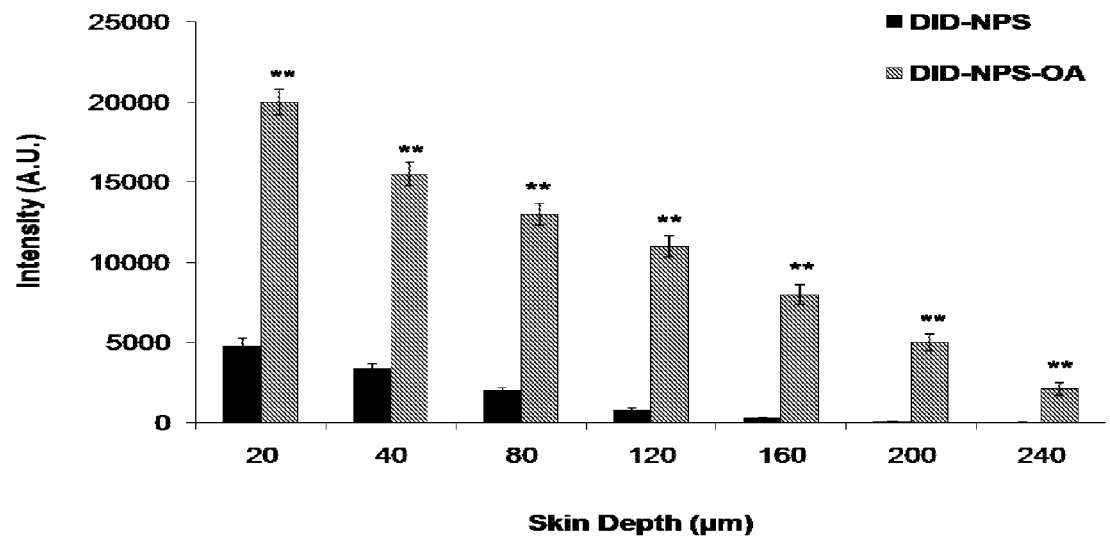

The Raman confocal spectroscopy results are summarized graphically in FIG. 8. According to FIG. 8, the fluorescence intensities of DID-NPS-OA were found to be higher than DID-NPS after 24 hours of skin permeation. At 80 μm skin depth, the intensities of fluorescence were 1,923 and 13,455 counts for DID-NPS and DID-NPS-OA treated samples, respectively. At 120 μm skin depth, the intensities were reduced to 780 and 11,243 counts for DID-NPS and DID-NPS-OA treated samples, respectively. The fluorescence signal for DID-NPS from 160 to 240 μm was below detection limit and was not detectable. However an intense signal was observed for DID-NPS-OA treated samples at a skin depth of 240 μm.

Example 3

A. Selection of Receiver Fluid

To maintain the sink condition, SP and KP were dissolved by gentle shaking in various receiver fluids, such as 10% v/v ethanol in PBS (pH 7.4), 0.1-0.5% w/v Volpo 20 in PBS (pH 7.4), 5% w/v BSA in PBS (pH 7.4). The final concentration of SP and KP in receiver fluid was 1 mg/ml.

For permeation studies, the use of specific receptor fluid was needed. Thus, the solubility test was done in selected receiver fluids. KP was soluble in 0.1% w/v Volpo 20 in PBS (pH 7.4). Though SP was insoluble in the same receiver fluid, SP was soluble in 0.5% w/v Volpo 20 in PBS (pH 7.4). SP and KP were both soluble in ethanol. However, when SP and KP were mixed together in PBS (pH 7.4) containing 10% w/v ethanol, precipitation was observed. SP and KP were soluble in 5% w/v BSA in PBS (pH 7.4). BSA may have interfered with the retention peak of SP and KP in HPLC analysis.

Also, excess amount of surfactant into the receiver fluid led to emulsification of skin, and thus resulted in oozing of skin components into the receiver fluid. These oozed components may have interfered with the retention peak of SP and KP. To avoid the interference, 0.5% w/v Volpo 20 in PBS (pH 7.4) was selected for skin permeation studies based on the solubility of SP and KP.

B. Human Skin Permeation Studies

Dermatomed human skin was obtained from ALLOSOURCE (Centennial, Colo.) in normal saline containing 10% glycerol with a thickness of 0.5±0.1 mm. Skin was then stored at −80° C. until use. The dermatomed skin was thawed and washed with water for thirty (30) minutes to remove excess glycerol.

Skin permeation studies were performed using established procedures. The dermatomed human skin was mounted on Franz diffusion cell set up (PERMEGEAR, Inc., Riegelsville, Pa.). The surface area of the dermatomed human skin exposed to the formulation in the donor chamber was 0.64 cm$^2$, and the receiver fluid volume was five (5) ml. The NPS and NPS-OA were applied evenly on the surface of the human skin in the donor compartment.

The skin permeation study was performed using six (6) diffusion cells and represented as an average of six (6) cells. The receiver compartment was filled with 0.5% w/v Volpo 20 in PBS (pH 7.4) and stirred at 300 rpm. The temperature of the receiver compartment was maintained at 32° C.±0.5° C. using a circulating water bath to simulate the skin temperature at physiological level.

To simulate the clinical conditions, a non-occlusive method was followed and the surface of the skin was exposed to the surrounding air. After 24 hours of skin permeation, the receiver fluid was collected and centrifuged at 13,500 rpm for fifteen (15) minutes and analyzed for drug content using HPLC.

Figure 9A:
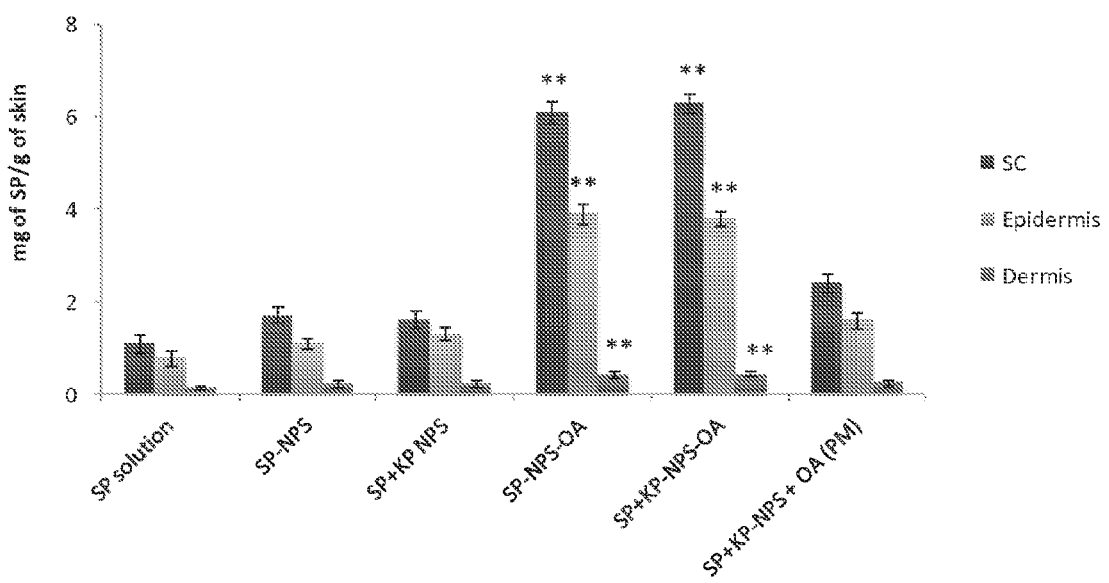
Figure 9B:
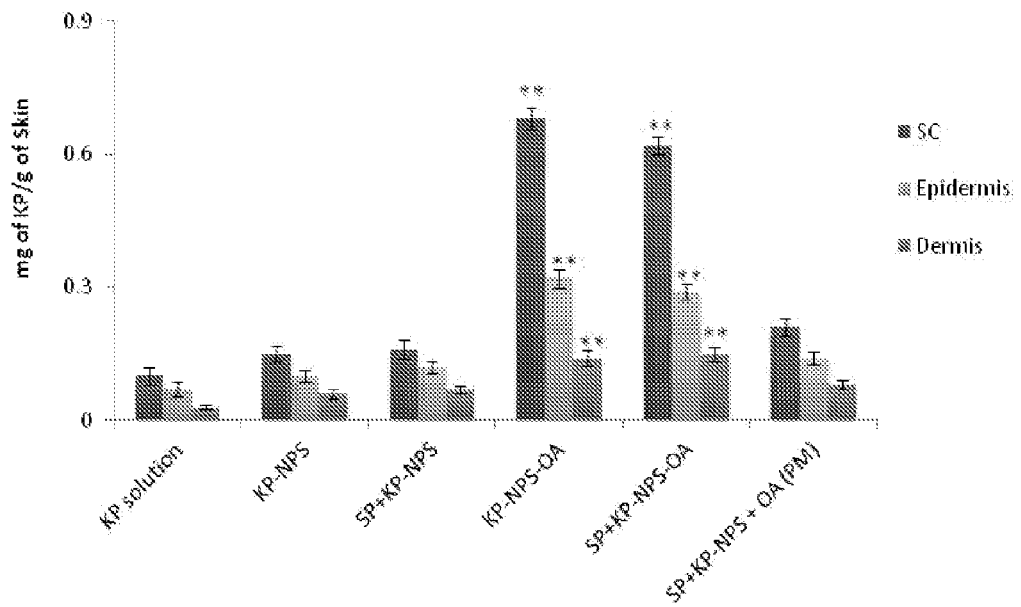
Figure 9C:
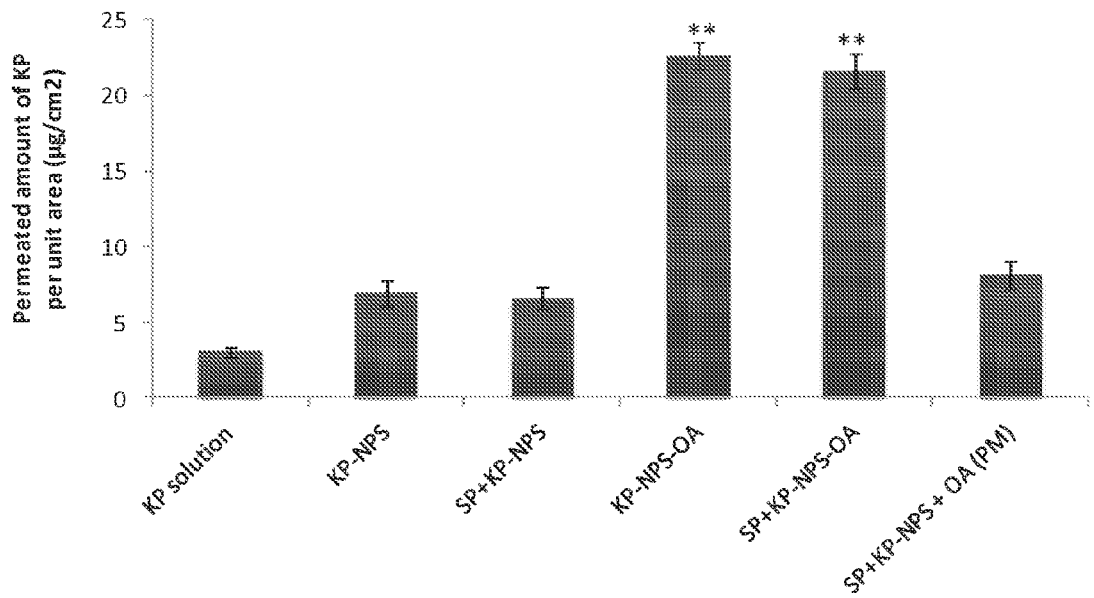

The detection of SP and KP levels in skin layers and in the receiver compartment was determined separately using two different analytical columns. FIGS. 9A-C show the effect of surface modification on skin permeation of NPS at the end of 24 hours with dermatomed human skin.

SP was below detection limits in the receiver compartment for any formulation. The SC, epidermal and dermal retention of SP for SP-NPS-OA was 6.30, 3.86 and 0.44 mg/g of skin, respectively. The skin retention of SP in various skin layers for SP-NPS-OA was approximately 5.7 and 3.7 times higher than SP-Solution and SP-NPS, respectively, seen in FIG. 9A.

The SC, epidermal and dermal retention of KP for KP-NPS was 0.68, 0.32 and 0.12 mg/g of skin, respectively. The retention of KP in various skin layers for KP-NPS-OA was approximately 6.8 and 4.1 times higher than KP-Solution and KP-NPS, respectively, seen in FIG. 9B. These experiments were performed in vitro using Franz diffusion cells on dermatomed human skin.

The skin biopsies had been collected and processed further to detect the amount of KP permeated in each layers of skin. For KP-NPS-OA, KP was detectable in the receiver compartment with 22.48 μg/cm$^2$ permeated through the skin after 24 hours. The permeated amount of KP was approximately 7 and 3.2 times higher than KP-Solution and KP-NPS, respectively, seen in FIG. 9C.

The skin retentions of SP and KP for SP-NPS-OA and KP-NPS-OA, respectively, were similar to SP+KP-NPS-OA for both drugs. This indicates that loading of combination of drugs in NPS did not affect the skin permeation characteristics of the individual drugs.

C. Drug Extraction from Skin

To detect the drug retention in dermatomed human skin layers, the dosing area (0.64 cm$^2$) was collected with a biopsy punch. The SC, epidermis and dermis were separated using cryotome. The SC, epidermis and dermis were each minced and boiled with 250 μl PBS (pH 7.4) for ten (10) minutes. To these samples, 250 μl of acetonitrile was added to solubilize the drug. All the samples were centrifuged at 13,500 rpm for twenty (20) minutes. The supernatant was collected and analyzed by HPLC for drug content.

Example 4

A. In Vitro Drug Release

In vitro drug release studies of KP-NPS, SP-NPS, SP+KP-NPS, KP-NPS-OA, SP-NPS-OA and SP+KP-NPS-OA were performed to investigate the amount of drug released from NPS or NPS-OA. A porous membrane of MWCO at 50,000 Da (SIGMA-ALDRICH Co., St. Louis, Mo.) was used. The membrane was mounted between the donor and receiver compartments of Franz diffusion cells (N. Ghouchi Eskandar, S. Simovic, C. Prestidge, Nanoparticle coated submicron emulsions: sustained in-vitro release and improved dermal delivery of All-trans-retinol, *Pharm Res*, 26 (2009) 1764-1775).

The NPS dispersion was applied evenly on the surface of the membrane in the donor compartment. The receiver compartment was filled with 0.5% w/v Volpo in PBS (pH 7.4), stirred at 300 rpm and maintained at 32° C.±0.5° C. At predetermined time intervals (e.g., 1, 2, 4, 6, 8, 12, 22, 24, 48 and 72 hours), 0.5 ml samples were collected from the receiver compartment and replaced with fresh buffer solution. The samples collected from receiver compartment were analyzed for drug content using the HPLC method.

During in vitro drug release studies, SP and KP were released in a controlled manner. SP showed 34% of release within 24 hours of NPS application, as depicted in FIG. 10A.

KP showed complete (>75%) release within 24 hours of NPS application, as depicted in FIG. 10B.

Initial burst release of KP from NPS and NPS-OA may have been observed due to un-entrapped KP available in NPS dispersion. Further, the controlled release of SP from NPS and NPS-OA might be due to the long diffusion path length which SP has to initiate from PLGA matrix to cross-link the chitosan coat of the NPS or NPS-OA.

There was no statistical difference between the drugs released from NPS or NPS-OA. This might be because of porous membranes. In addition, drug release from NPS comprising single and combination drugs (KP-NPS or SP-NPS and SP+KP-NPS) was unaffected, confirming no interaction between KP and SP. This also indicates the ability for combination therapies in certain embodiments of the present invention.

Generally zero order, first order, Korsmeyer-Peppas, Hixson-Crowell and Higuchi equations are used in determining the release kinetics of polymeric nanoparticles. The release pattern of KP from NPS or NPS-OA may follow Korsmeyer-Peppas kinetics with a best fit $r^2$ value of 0.98, where first order, Hixson-Crowell and Higuchi equations yield or best fit $r^2$ values of 0.89, 0.78 and 0.92, respectively.

Similarly the release pattern of SP from NPS or NPS-OA follows Korsmeyer-Peppas kinetics with a best fit $r^2$ value of 0.9987, where first order, Hixson-Crowell and Higuchi equations yield or best fit $r^2$ values of 0.98, 0.9975 and 0.95, respectively.

B. HPLC Analysis

An HPLC system (WATERS Corp., Milford, Mass.) with a Vydac reverse phase C18 (300 Å pore size silica) analytical column (5 μm, 4.6×250 mm) (GRACEVYDAC, Columbia, Md.) was used for the analysis of SP. The mobile phases used for SP were 0.1% v/v TFA in water (solvent A) and 0.1% v/v TFA in acetonitrile (solvent B). They were run at a gradient of 60:40 to 40:60 (solvent A:B, respectively) for twenty (20) minutes, with a flow rate of 1.2 ml/minute. SP content in the samples was determined at 230 nm.

A WATERS SYMMETRY C18 analytical column (5 μm, 4.6×250 mm) was used for analysis of KP. The mobile phases used were 0.025% v/v TFA in water (solvent A) and 0.025% v/v TFA in acetonitrile (solvent B). They were run at a gradient of 70:30 for five (5) minutes, followed by 10:90 for eight (8) minutes, followed by 0:100 (solvent A:B, respectively) with a flow rate of 1 ml/minute. KP content in the samples was determined at 255.5 nm.

Example 5

A. In Vivo Model for Allergic Contact Dermatitis (ACD)

To investigate the effect of surface modification of NPS with OA in vivo, an allergic contact dermatitis (ACD) model was developed. Reduction in ear thickness was evaluated as a response. DNFB-induced edema (after secondary exposure) is widely used for investigating cutaneous inflammatory process (L. Kikwai et al., In vitro and in vivo evaluation of topical formulations of spantide II, AAPS PharmSciTech, 6 (2005) E565-572). The effect of NPS and NPS-OA on inflammation was investigated using DNFB-induced ACD model.

C57BL/6 mice were sensitized on day zero by applying 25 μl of 0.5% v/v DNFB in acetone:olive oil (4:1) on the shaved abdomen. The mice were then challenged on day 5 by epicutaneous application of 25 μl of 0.2% DNFB in acetone:olive oil (4:1) on the right ear in order to induce an ACD response. The left ears were treated with vehicle alone (acetone:olive oil 4:1) and served as an internal control.

The ACD response was determined by the degree of ear swelling compared with that of the vehicle treated contralateral ear before DNFB challenge. The increase in ear thickness was measured with a vernier caliper (Fraction+Digital Fractional Caliper, GENERAL TOOLS & INSTRUMENTS Co., LLC., New York, N.Y.) at various time intervals (e.g., 0, 24, 48 and 72 hours). Right ears of the mice were treated with topical application of KP-Solution, SP-Solution and SP+KP-Solution, KP-NPS, SP-NPS, SP+KP-NPS, KP-NPS-OA, SP-NPS-OA and SP+KP-NPS-OA, two (2) hours after antigen challenge and three (3) times a day thereafter for three (3) days. Dexamethasone, 0.5 mM solution in ethanol and PEG-400 mixture were used as a positive control.

Ear swelling was measured before the application of drug solution, NPS or NPS-OA to the mice. This was considered as 0-hour ear thickness. Then the drug solution, NPS or NPS-OA was applied and the ear thickness was measured at 24, 48, and 72 hours. The ACD response was determined by taking a difference between 0-hour ear thickness and subsequent time points (24, 48, and 72 hours).

Combination Index (CI) value (M. Chougule, et al., Anticancer activity of noscapine, an opioid alkaloid in combination with Cisplatin in human non-small cell lung cancer, *Lung Cancer*, 71 (2011) 271-282) was used to evaluate the combined effect of SP and KP. The CI was calculated using following equation:

$$\text{Combination Index}(CI) = \frac{\text{Response of Ketoprofen}}{\text{Response of Combination}} + \frac{\text{Response of Spantide } II}{\text{Response of Combination}}$$

A CI value greater than 1.3 was considered antagonistic; a CI between 1.1 and 1.3 was considered moderately antagonistic; a CI between 0.9 and 1.1 was considered to have additive effect; a CI between 0.8 and 0.9 was considered slightly synergistic; a CI between 0.6 and 0.8 was considered moderately synergistic; a CI between 0.4 and 0.6 was considered synergistic; and a CI between 0.2 and 0.4 was considered strongly synergistic.

Histological sections of mice ears were observed after hematoxylin and eosin (H&E) staining with an optical microscope (OLYMPUS AMERICA, Melville, N.Y.) using a 10× lens.

The reduction of ear swelling in mice was used to monitor the treatment of inflammation after application of the various solutions and formulations. The effect of KP-, SP- and SP+KP-Solutions, KP-NPS, SP-NPS, SP+KP-NPS, KP-NPS-OA, SP-NPS-OA, and SP+KP-NPS-OA on the reduction of ear swelling is shown in FIG. 11.

The ear thickness increased from 122.48 to 143.42 μm with time for control animals. There was no statistical difference in ear thickness before and after application of dexamethasone. However, at 72 hours, ear thickness decreased to 98.74 μm, 91.76 μm and 73.45 μm for KP-Solution, KP-NPS and KP-NPS-OA, respectively. Similarly ear thickness decreased to 108.15 μm, 98.56 μm and 80.23 μm for SP-Solution, SP-NPS and SP-NPS-OA, respectively.

The ear thickness for SP+KP-Solution, SP+KP-NPS and SP+KP-NPS-OA was 66.78 μm, 48.59 μm and 29.34 μm, respectively. In addition, the CI value calculated using ACD model for SP+KP-Solution was 0.92, indicating additive effect, while for SP+KP-NPS-OA the CI value was 0.76, indicating moderate synergism.

The response of ACD model was further characterized by histological examination. The results are depicted in FIG. 12. The combination of SP+KP-NPS-OA was more effective in the treatment of ACD by reducing the ear swelling, compared to control, SP+KP-NPS and SP+KP Solution.

B. Statistical Analysis

The SP and KP content of the skin tissue was expressed as milligrams per gram of the tissue. Differences between the skin permeation and ACD response of SP+KP Solution, SP+KP-NPS and SP+KP-NPS-OA were examined using ANOVA and Tukey multiple comparison test. Means were compared between two groups by t test and between three dose groups by one-way variance analysis (ANOVA). Mean differences with $p<0.001$ were considered to be significant.

Example 6

A. Preparation of Bilayered Hybrid Nanostructured Lipid Carriers (H-NLC)

H-NLCs were prepared by modified hot melt homogenization technique (R. R. Patlolla et al., Translocation of cell penetrating peptide engrafted nanoparticles across skin layers, *Biomaterials*, 2010; 31:5598-607). Phosphatidyl choline, SP and KP were dispersed in ethanol. To this, miglyol was added. Ethanol was evaporated by applying mild heating. To this, a mixture of PRECIROL and MONOSTEROL were added with constant heating in a water bath maintained at 50-60° C. to melt the lipids.

Water phase was prepared separately by dissolving LUTROL F68 (poloxamer 188), followed by dispersing span 80 in water. This water phase was also brought to the same temperature as that of the lipid phase. Further the water phase was added to the lipid phase under high speed mixing (20,000 rpm for thirteen (13) minutes).

To these SP+KP-NLCs, a gelatin solution was added. Capsaicin was dispersed in the glutaraldehyde and added drop wise to the SP+KP-NLCs containing gelatin solution. This resulted in crosslinking of gelatin with entrapment of capsaicin in the gelatin matrix.

B. Surface Modification of H-NLC

The free amino groups of the gelatin were then modified with succinimidyl ester of OA-PEG after two (2) to four (4) hours of incubation at room temperature, using a substantially similar procedure described in Example 2, subsection D.

C. Human Skin Permeation Studies

The skin permeation of H-NLC was performed using dermatomed human skin in a substantially similar procedure described in Example 3, subsection B.

Example 7

A. Preparation of Bilayered Hybrid Micelles

The hybrid micelles were prepared by a co-solvent evaporation method. SP and KP were dissolved in acetone, and mixed with PEG-PLA, DOPE and DSPE-PEG in acetone. The organic solution was added drop wise every five (5) seconds, using a peristaltic pump, into four (4) mL of deionized water under continuous stirring. Acetone was then slowly removed by evaporation (with stirring) in a desiccator under vacuum (2 hours, 200 mbar). The final micelle concentration was adjusted by adding deionized water containing paracetamol. After overnight equilibration, the solution was centrifuged at 9500×g for fifteen (15) minutes to remove the non-incorporated drug.

B. Surface Modification of Bilayered Hybrid Micelle

The free amino groups of the DOPE were then modified with succinimidyl ester of OA-PEG after two (2) to four (4) hours of incubation at room temperature, using a substantially similar procedure described in Example 2, subsection D.

C. Human Skin Permeation Studies

The skin permeation of H-NLC was performed using dermatomed human skin in a substantially similar procedure described in Example 3, subsection B.

Example 8

A. Preparation of Nanoparticles

NPS were prepared using a substantially similar procedure as described in Example 2, subsection C.

B. Surface Modification of Nanoparticles

Modification of the NPS was conducted using a substantially similar procedure as described in Example 2, subsection D.

C. Preparation of Carrier Containing Surface Modified Nanoparticles

NPS were then mixed with at least one carrier agent using any method or carrier agent known in the art, thus formulating a carrier for delivering the NPS to the skin of a patient in need thereof. Examples of formulated carriers include, but are not limited to, aqueous dispersions, gels, lotions, powders, liniments, ointments, creams, patches, among other suitable delivery mechanisms for the NPS.

In certain embodiments, the carrier agent may be a gelling agent, allowing the NPS to be delivered via a nanogel to the skin of a patient in need thereof. Nanogels are nano-sized networks of chemically or physically cross linked polymer particles. Nanogels can aid in creating a uniform dispersion of the NPS in the matrix and increases the contact time, resulting in enhanced skin penetration of the drug payload. Any suitable gelling or thickening agent may be used to create this carrier. Examples of suitable thickening agents or gelling agents include, but are not limited to, gelatin, carboxymethyl cellulose, carrageenan, carbomer, acacia, agar, xanthan gum, tragacanth, guar gum, alginates, gum arabic, starch, tragacanth, bovine albumin serum, chitosan, hydroxyethyl cellulose, hydroxypropyl cellulose, hydroxypropyl methyl cellulose, methyl cellulose, ethyl cellulose, polyacrylic acid, carbopol, bentonite, pectin, psyllium seed gum, polyvinyl alcohol, polyvinylpyrrolidone, polymethacrylate, polyacrylate, polyacrylamide, polyethylene glycol, poloxamer, polycarbophil, polyethylene oxide, polyester, polyurea, and polyamide, among other suitable thickening or gelling agents.

D. Human Permeation Studies The skin permeation of NPS was performed using dermatomed human skin in a substantially similar procedure described in Example 3, subsection B.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

It is also to be understood that the following claims are intended to cover all of the generic and specific features of the invention herein described, and all statements of the scope of the invention that, as a matter of language, might be said to fall therebetween.

What is claimed is:

1. A composition for dermal delivery of at least one pharmaceutical agent through a stratum corneum of a subject, comprising each of the at least one pharmaceutical agent admixed with at least one layer of nanostructures, wherein the at least one layer of nanostructures to facilitate penetration of the composition through the stratum corneum of the subject has structure of formula I

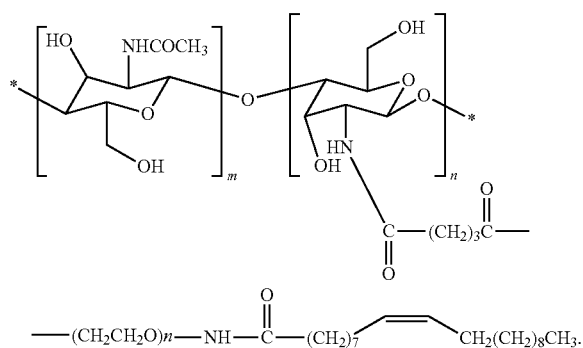

Formula I

2. The composition of claim 1, wherein the at least one pharmaceutical agent is selected from the group consisting of spantide II, cyclosporine A, alpha-MSH, capsaicin and ketoprofen.

3. The composition of claim 1, further comprising at least one polymer.

4. The composition of claim 3, wherein the at least one polymer is PLGA.

5. The composition of claim 1, further comprising at least one lipid.

6. The composition of claim 5, wherein the at least one lipid is a derivative of glycerol.

7. The composition of claim 1, further comprising an emulsifying agent.

8. The composition of claim 7, wherein the emulsifying agent is polyvinyl alcohol.

9. The composition of claim 1, further comprising a surfactant.

10. The composition of claim 9, wherein the surfactant is polyoxyethylene (20) sorbitan monooleate.

11. The composition of claim 1, further comprising an anti-foaming agent.

12. The composition of claim 11, wherein the anti-foaming agent is sorbitan monooleate.

13. The composition of claim 1, further comprising a cross-linking agent.

14. The composition of claim 13, wherein the cross-linking agent is selected from the group consisting of sodium tripolyphosphate and glutaraldehyde.

15. A carrier for dermal delivery of at least one pharmaceutical agent through a stratum corneum of a subject, comprising each of the at least one pharmaceutical agent and at least one layer of nanostructures with structure of formula I in claim 1 to facilitate penetration of the composition through the stratum corneum, admixed with a carrier agent, whereby the carrier is formulated.

16. The carrier of claim 15, wherein the formulated carrier is selected from the group consisting of aqueous dispersions, nanogels, lotions, powders, emulsion, liniments, ointments, creams and patches.

17. A composition for dermal delivery of at least one pharmaceutical agent, comprising:

the at least one pharmaceutical agent, wherein the at least one pharmaceutical agent is spantide II;

at least one layer of nanostructures with structure of formula I in claim 1;

at least one polymer, wherein the at least one polymer is PLGA;

at least one lipid, wherein the at least one lipid is glycerol distearate;

an emulsifying agent, wherein the emulsifying agent is polyvinyl alcohol;

a surfactant, wherein the surfactant is polyoxyethylene (20) sorbitan monooleate;

an anti-foaming agent, wherein the anti-foaming agent is sorbitan monooleate; and a cross-linking agent, wherein the cross-linking agent is sodium tripolyphosphate.

* * * * *